US009256930B2

(12) United States Patent
Suzuki

(10) Patent No.: US 9,256,930 B2
(45) Date of Patent: Feb. 9, 2016

(54) X-RAY INSPECTION METHOD AND DEVICE

(75) Inventor: Yoshikuni Suzuki, Shizuoka-ken (JP)

(73) Assignee: Yamaha Hatsudoki Kabushiki Kaisha, Shizuoka-ken (JP)

( * ) Notice: Subject to any disclaimer, the term of this patent is extended or adjusted under 35 U.S.C. 154(b) by 0 days.

(21) Appl. No.: 14/353,479

(22) PCT Filed: Nov. 9, 2011

(86) PCT No.: PCT/JP2011/006267
§ 371 (c)(1),
(2), (4) Date: Apr. 22, 2014

(87) PCT Pub. No.: WO2013/069057
PCT Pub. Date: May 16, 2013

(65) Prior Publication Data
US 2015/0243012 A1 Aug. 27, 2015

(51) Int. Cl.
*G06K 9/00* (2006.01)
*G06T 7/00* (2006.01)
*G01B 15/04* (2006.01)
*G01N 23/04* (2006.01)
*G06T 11/00* (2006.01)

(52) U.S. Cl.
CPC .............. *G06T 7/0002* (2013.01); *G01B 15/04* (2013.01); *G01N 23/04* (2013.01); *G01N 23/046* (2013.01); *G06T 11/006* (2013.01); *G01B 2210/56* (2013.01); *G01N 2223/6113* (2013.01); *G06T 2207/30108* (2013.01); *G06T 2211/436* (2013.01)

(58) Field of Classification Search
None
See application file for complete search history.

(56) References Cited

U.S. PATENT DOCUMENTS

| 5,592,562 | A | * | 1/1997 | Rooks | 382/150 |
| 5,978,440 | A | * | 11/1999 | Kang et al. | 378/21 |
| 6,009,145 | A | * | 12/1999 | Zweig et al. | 378/58 |
| 6,151,380 | A | * | 11/2000 | Zweig et al. | 378/58 |
| 6,215,843 | B1 | * | 4/2001 | Saito et al. | 378/19 |
| 6,292,530 | B1 | | 9/2001 | Yavus et al. | |

(Continued)

FOREIGN PATENT DOCUMENTS

| CN | 1595124 A | 3/2005 |
| CN | 1932492 A | 3/2007 |

(Continued)

OTHER PUBLICATIONS

International Search Report; PCT/JP2011/006267; Feb. 14, 2012.

(Continued)

*Primary Examiner* — Aaron W Carter
(74) *Attorney, Agent, or Firm* — Studebaker & Brackett PC

(57) ABSTRACT

A first X-ray image is obtained by imaging a target in a first direction and at a first elevation angle, and a second X-ray image is obtained by imaging the target in a second direction and at a second elevation angle. Based on these two X-ray images, cross-section data of the target is obtained. The first and second X-ray images are converted into first and second thickness data, and first cross-section data based on a first surface side of the target and second cross-section data based on a second surface side of the target are obtained based on the first thickness data. Similar third cross-section data and four cross-section data are obtained based on the second thickness data. The cross-section data of the target is obtained by partially extracting and synthesizing cross-section data of a highly reliable region from these pieces of cross-section data.

9 Claims, 21 Drawing Sheets

(56) References Cited

U.S. PATENT DOCUMENTS

| | | | |
|---|---|---|---|
| 6,337,445 B1 * | 1/2002 | Abbott et al. | 174/260 |
| 6,442,234 B1 * | 8/2002 | Morken et al. | 378/58 |
| 6,823,040 B1 * | 11/2004 | Teraoka | 378/25 |
| 6,996,265 B1 | 2/2006 | Patnaik | |
| 7,013,038 B1 | 3/2006 | Patnaik | |
| 2004/0047448 A1 * | 3/2004 | Kerschner | 378/98.8 |
| 2005/0074088 A1 | 4/2005 | Ichihara et al. | |
| 2006/0188141 A1 | 8/2006 | Patnaik | |
| 2008/0130983 A1 | 6/2008 | Patnaik | |
| 2009/0080764 A1 * | 3/2009 | Srinivasan et al. | 382/150 |
| 2010/0177947 A1 * | 7/2010 | Hayashi et al. | 382/132 |
| 2011/0222655 A1 * | 9/2011 | Murakami et al. | 378/54 |

FOREIGN PATENT DOCUMENTS

| | | |
|---|---|---|
| JP | 6336137 A | 2/1988 |
| JP | 04-359447 A | 12/1992 |
| JP | 2000-350721 A | 12/2000 |
| JP | 2000-352559 A | 12/2000 |
| JP | 2002-162370 A | 6/2002 |
| JP | 2004-294120 A | 10/2004 |
| JP | 3665294 B2 | 6/2005 |
| JP | 3942786 B2 | 7/2007 |
| JP | 2008-268026 A | 11/2008 |
| JP | 2009-162596 A | 7/2009 |
| JP | 2010-127810 A | 6/2010 |
| JP | 2011-169791 A | 9/2011 |

OTHER PUBLICATIONS

The extended European search report issued by the European Patent Office on Mar. 11, 2015, which corresponds to European Patent Application No. 11875360.7-1558 and is related to U.S. Appl. No. 14/353,479.

Asaad F. Said et al.; "Automated Detection and Classification of Non-Wet Solder Joints"; IEEE Transactions on Automation Science and Engineering; Jan. 2011; pp. 67-80; vol. 8, No. 1; IEEE Service Center; NY, USA.

S.M. Rooks et al.; "Development of an Inspection Process for Ball-Grid-Array Technology Using Scanned-Beam X-ray Laminography"; IEEE Transactions on Components, Packaging, and Manufacturing Technology; XP000542890; Dec. 1995; pp. 851-860; Part A; vol. 18; No. 4; IEEE Service Center, NJ, USA.

* cited by examiner

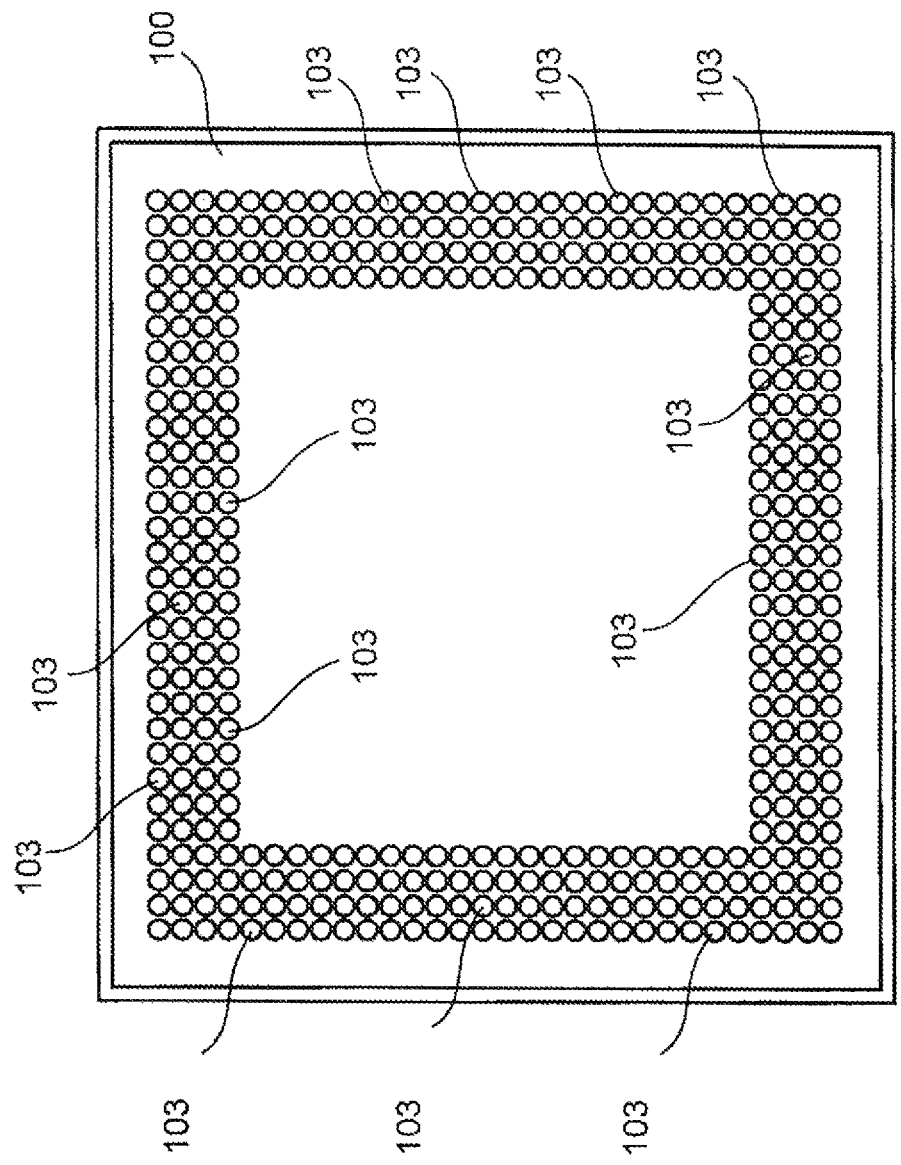

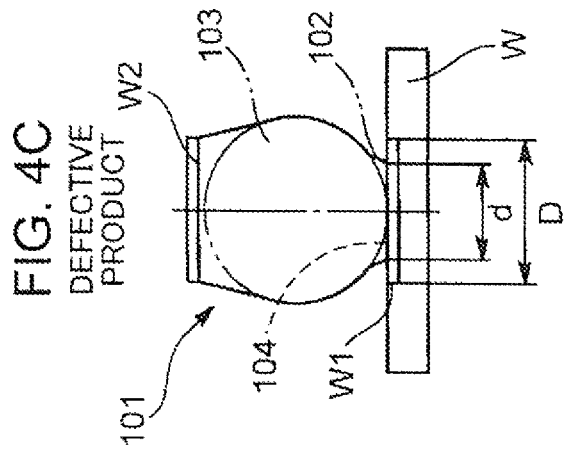
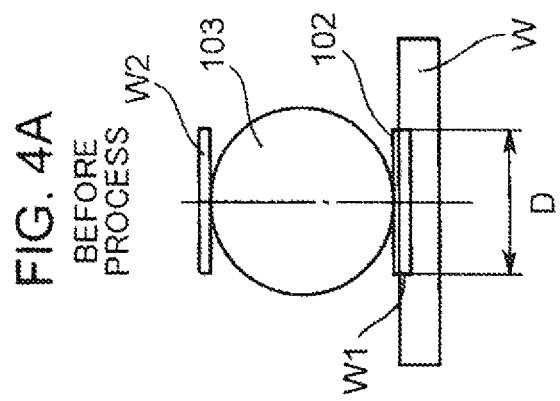
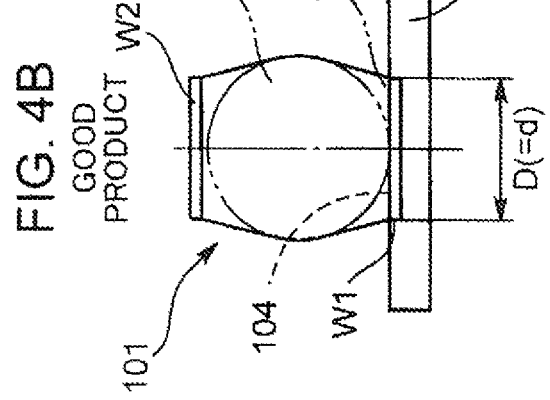

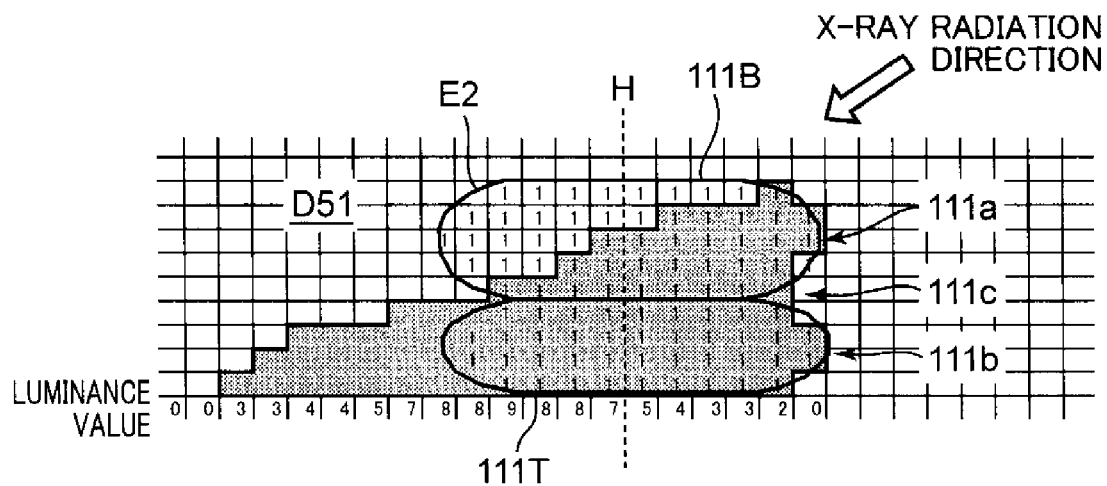
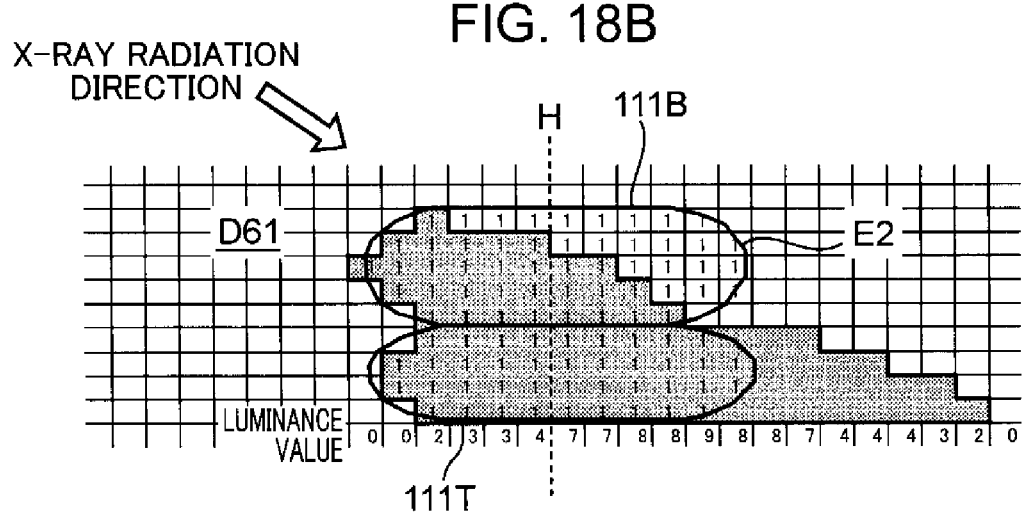
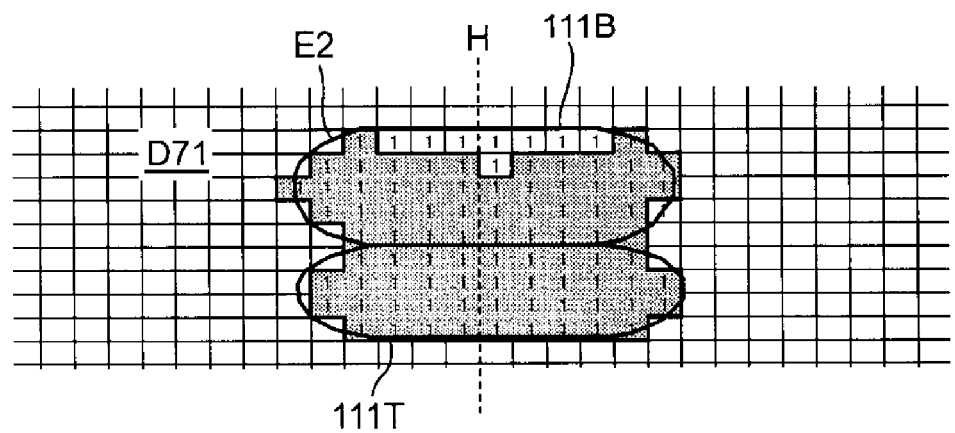

X-RAY INSPECTION METHOD AND DEVICE

CROSS REFERENCE TO RELATED APPLICATIONS

This application claims benefit of priority to International Patent Application No. PCT/JP2011/006267 filed on Nov. 9, 2011, the entire content of which is incorporated herein by reference.

TECHNICAL FIELD

The present technical field relates to an X-ray inspection method and device for obtaining cross-section data of a three-dimensional target by transmitting X-rays through the target.

BACKGROUND

At present, an X-ray inspection is used for a wide range of industrial products. The X-ray inspection is used also for a printed circuit board on which various electronic components are mounted. For example, an inspection, as to whether or not a BGA (Ball Grid Array), which is an ultra-small LSI component, is properly soldered to a board is made using X-rays. Generally, the BGA includes a solder ball terminal on an electrode pad thereof and is held in a state where the solder ball terminal is held in contact with a solder layer formed on a board-side electrode pad and, subsequently, a heating process is applied to melt solder balls (and the solder layer) to fix the BGA to the board. In the X-ray inspection, data on cross-sectional shapes of the melted solder balls is obtained. This is because the solder ball is deformed into a barrel shape by the heating process in a normal state, whereas it is deformed into a shape different from the barrel shape in a defective state.

An X-ray CT (Computed Tomography) method is known as an X-ray inspection method aimed at boards as described above. For example, Japanese Patent Publication No. 3665294 discloses an X-ray inspection method utilizing vertical slice imaging. In this inspection method, a multitude of horizontal slice images of a melt of the solder ball are imaged and a vertical slice image of the melt of the solder ball is formed utilizing these. However, this method requires several tens of X-ray images to be obtained for one inspection target, wherefore there are problems that it takes time for an imaging operation and an X-ray exposure dose of an inspection target increases.

Further, Japanese Unexamined Patent Publication No. 2010-127810 discloses an X-ray inspection method for obtaining a three-dimensional X-ray CT image by iteration using a plurality of X-ray sources and X-ray detectors. According to this method, a three-dimensional shape of an inspection target can be obtained, but an enormous number of X-ray images are necessary. Thus, an imaging time and an X-ray exposure dose of the inspection target are a problem similarly to the above case.

SUMMARY

An object of the present disclosure is to provide X-ray inspection method and device capable of precisely obtaining cross-sectional data of an inspection target based on as few X-ray images as possible.

One aspect of the present disclosure is directed to an X-ray inspection method for computing a cross-sectional shape of a three-dimensional target having a first surface and a second surface facing the first surface by transmitting X-rays through the target using an X-ray source for radiating X-rays, an X-ray detector for detecting the X-rays and a computing device, comprising:

arranging the X-ray source in a predetermined first direction and at a predetermined first elevation angle with respect to the target and the X-ray detector to face the X-ray source across the target and, in this state, causing the X-rays to be radiated from the X-ray source and the X-ray detector to obtain a first X-ray image of the target;

arranging the X-ray source in a predetermined second direction different from the first direction and at a predetermined second elevation angle with respect to the target and the X-ray detector to face the X-ray source across the target and, in this state, causing X-rays to be radiated from the X-ray source and the X-ray detector to obtain a second X-ray image of the target;

causing the computing device to compute first thickness data of the target viewed in the first direction and in a direction of the first elevation angle based on a luminance value distribution of the first X-ray image along the first direction and further compute first cross-section data based on the first surface side of the target and second cross-section data based on the second surface side based on the first thickness data;

causing the computing device to compute second thickness data of the target viewed in the second direction and in a direction of the second elevation angle based on a luminance value distribution of the second X-ray image along the second direction and further compute third cross-section data based on the first surface side of the target and fourth cross-section data based on the second surface side based on the second thickness data; and causing the computing device to partially extract cross-section data of a highly reliable region determined by the first and second directions from the first to fourth cross-section data and derive cross-section data of the target by synthesizing the extracted pieces of partial cross-section data.

Another aspect of the present disclosure is directed to an X-ray inspection device for computing a cross-sectional shape of a three-dimensional target having a first surface and a second surface facing the first surface by transmitting X-rays through the target, comprising:

an X-ray source for radiating X-rays;

an X-ray detector for detecting the X-rays radiated from the X-ray source and transmitted through the target and obtaining an X-ray image;

a drive controller for controlling the operation of the X-ray source and the X-ray detector;

an image processor for computing thickness data of the target based on a luminance value distribution of the X-ray image and computing cross-section data of the target based on the thickness data; and a determiner for determining whether or not the shape of the target is good based on the cross-section data;

wherein:

the drive controller:

causes the X-ray source to be arranged in a predetermined first direction and at a predetermined first elevation angle with respect to the target, causes the X-ray detector to be arranged to face the X-ray source across the target and, in this state, causes the X-rays to be radiated from the X-ray source and causes the X-ray detector to obtain a first X-ray image of the target, and subsequently causes the X-ray source to be arranged in a second direction different from the first direction and at a predetermined second elevation angle with respect to the target, causes the X-ray detector to be arranged to face the X-ray source across the target and, in this state, causes X-rays to be radiated from the X-ray source and causes the X-ray detector to obtain a second X-ray image of the target; and the image processor:

computes first thickness data of the target viewed in the first direction and in a direction of the first elevation angle based on a luminance value distribution of the first X-ray image along the first direction and further computes first cross-section data based on the first surface side of the target and second cross-section data based on the second surface side based on the first thickness data, subsequently computes second thickness data of the target viewed in the second direction and in a direction of the second elevation angle based on a luminance value distribution of the second X-ray image along the second direction and further computes third cross-section data based on the first surface side of the target and fourth cross-section data based on the second surface side based on the second thickness data, and further partially extracts cross-section data of a highly reliable region determined by the first and second directions from the first to fourth cross-section data and derives the cross-section data of the target by synthesizing the extracted pieces of partial cross-section data.

An object, features and advantages of the present disclosure will become more apparent upon reading the following detailed description along with the accompanying drawings.

BRIEF DESCRIPTION OF THE DRAWINGS

FIG. 3 is a plan view of an electronic component with parts to be inspected.

FIGS. 4A, 4B and 4C are side views showing a solder ball as an inspection target, wherein FIG. 4A shows a state before a heating process, FIG. 4B shows a good product after the heating process and FIG. 4C shows a defective product after the heating process.

FIGS. 6A and 6B are diagrams showing highly reliable regions of an X-ray image in the case of radiation of X-rays in a first direction, wherein FIG. 6A shows a target and FIG. 6B shows an X-ray image thereof.

FIGS. 7A and 7B are diagrams showing highly reliable regions of an X-ray image in the case of radiation of X-rays in a second direction, wherein FIG. 7A shows a target and FIG. 7B shows an X-ray image thereof.

FIGS. 18A and 18B are diagonal bar graphs showing examples of cross-section data and FIG. 18C is a graph showing a synthesis example of these pieces of cross-section data.

DETAILED DESCRIPTION

Figure 1:
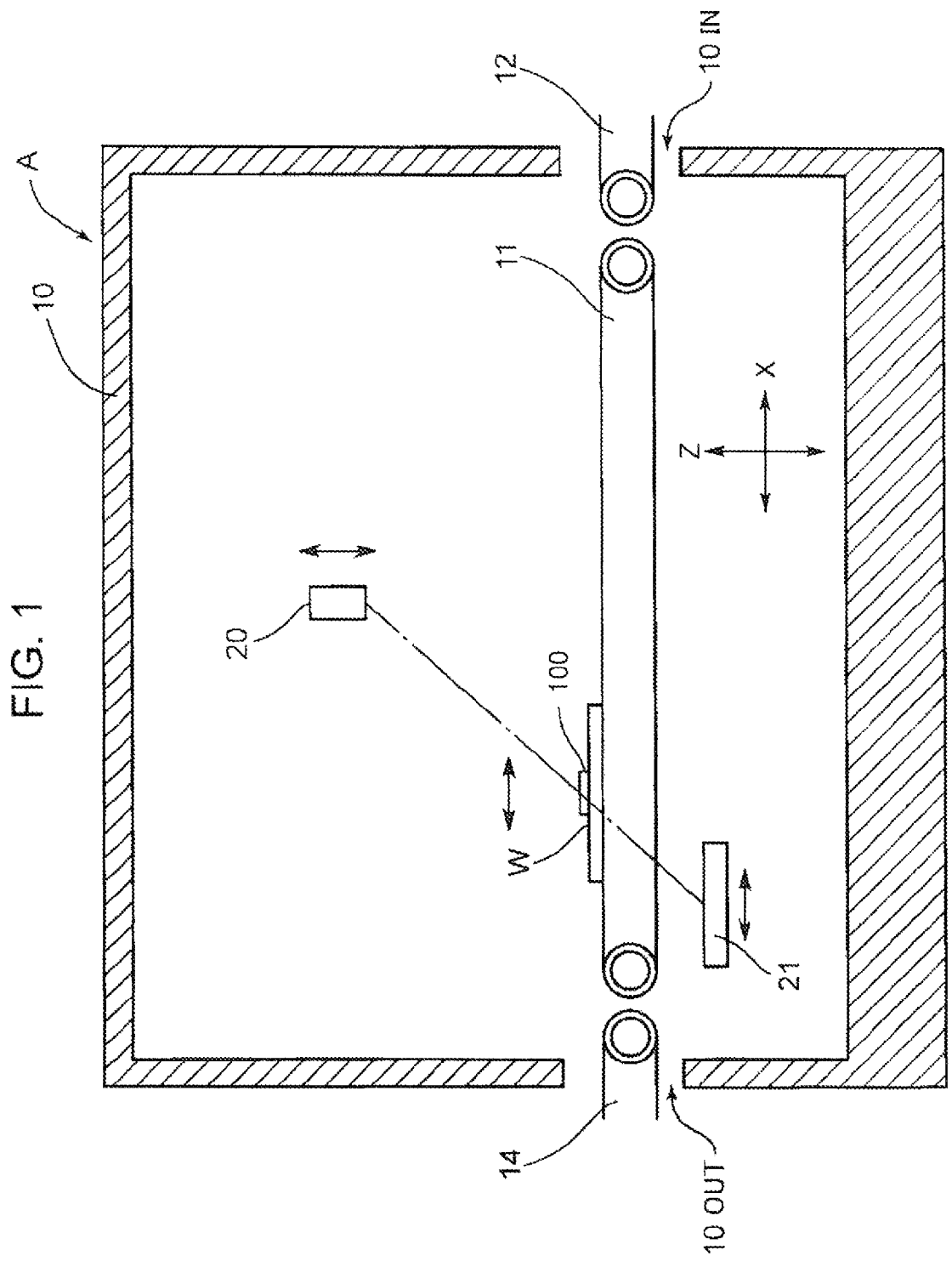
FIG. 1 is a sectional view schematically showing an X-ray inspection device according to an embodiment of the present disclosure.
Figure 2:
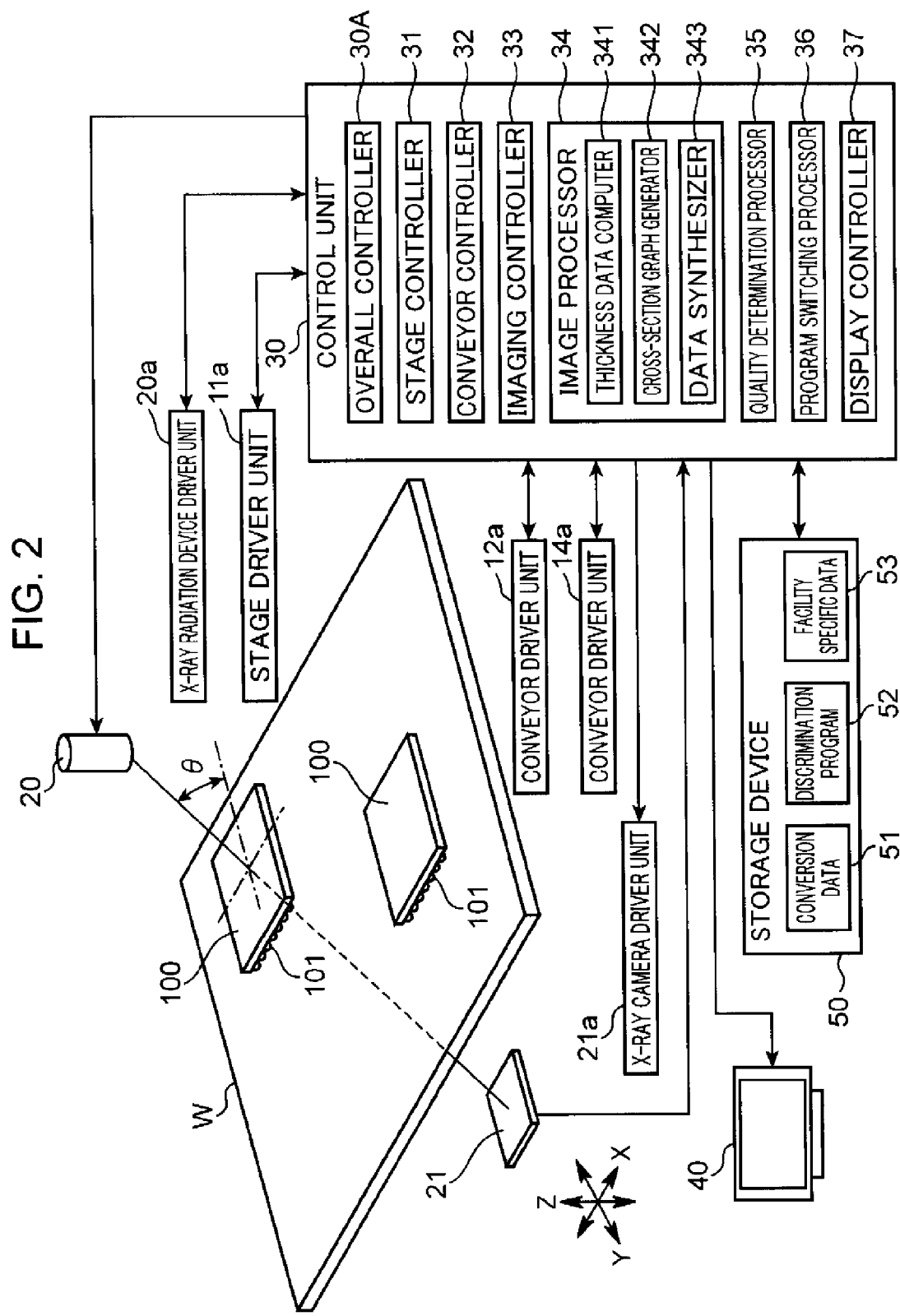
FIG. 2 is a block diagram showing a functional configuration of the X-ray inspection device.

Hereinafter, an embodiment of the present disclosure is described with reference to the accompanying drawings. FIG. 1 is a sectional view schematically showing an X-ray inspection device A according to the embodiment of the present disclosure, and FIG. 2 is a block diagram showing a functional configuration of the X-ray inspection device A. The X-ray inspection device A is an inspection device for inspecting a joint state of a BGA (Ball Grid Array; an example of an electronic component) 100 and a printed circuit board W after a reflow process. The BGA 100 is one type of an IC package for surface mounting.

FIG. 3 is a plan view of the BGA 100. The BGA 100 includes a multitude of solder balls 103 on a lower surface thereof. The solder balls 103 are provided in a predetermined array on a peripheral part of the BGA 100 and, after being melted by a so-called reflow process (heating process) and solidified, physically and electrically connect the BGA 100 and the printed circuit board W as a solder portion 101 (three-dimensional target/solder connecting portion). In a shown example, the BGA 100 includes 416 electrodes and the solder portion 101 connects these electrodes and the board W. The solder balls 103 are not necessarily provided on all the electrodes of the BGA 100, but selectively arranged (e.g. on 300 electrodes) based on a use mode of the BGA 100 and connect the BGA 100 to the printed circuit board W.

FIGS. 4A to 4C are side views showing the solder ball 103 or the solder portion 101 as a melt of the solder ball 103, wherein FIG. 4A shows a state before the reflow process, FIG. 4B shows a good product after the reflow process and FIG. 4C shows a defective product after the reflow process. The solder portion 101 is formed on the printed circuit board W by way of a printing process, a mounting process and the reflow process. The printing process includes a step of printing solder 102 (cream solder) on a land W1 provided on the printed circuit board W. The mounting process includes a step of mounting the BGA 100 on the printed solder 102. The reflow process includes a step of heating the printed circuit board W mounted with the BGA 100 in a melting furnace.

As shown in FIG. 4A, the solder ball 103 is interposed between the solder 102 and an electrode W2 of the BGA 100 while maintaining its spherical shape before the reflow process. On the other hand, after the reflow process, the solder 102 and the solder ball 103 are heated and fused together to be integrally solidified as shown in FIG. 4B. This solidified solder serves as the solder portion 101. The electrical and physical connection of the land W1 of the printed circuit board W and the electrode W2 of the BGA 100 is realized by the thus solidified solder portion 101.

Here, as shown in FIG. 4B, a joint surface 104 of the solder portion 101 with the land W1 or the electrode W2 is finished to have a joint width d equal to a land width D in a good product. However, there are not a few defective products in which the joint width d is shorter than the land width D. There can be, for example, cases where the joint width d is narrow as shown in FIG. 4C or the solder ball 103 is not joined at all. Needless to say, a shortage of strength and a connection failure can occur in such cases. Accordingly, the X-ray inspection device A of this embodiment is used to determine whether the individual solder portion 101 is good or defective.

The X-ray inspection device A images X-ray images of the solder portions 101, obtains a vertical cross-sectional shape of each solder portion 101 from the image data and discriminates whether each solder portion 101 is a good product or a defective product. With reference to FIGS. 1 and 2, the X-ray inspection device A includes a housing 10, a stage 11 housed in this housing 10, an X-ray radiation device 20 (X-ray source), an X-ray camera 21 (X-ray detector), and a control unit 30 (computing device) and a display unit 40 arranged at suitable positions outside the housing 10.

The housing 10 is a box-shaped casing provided with an X-ray shielding function and configured to house the stage 11 mentioned above, the X-ray radiation device 20 and the X-ray camera 21 as described above, and includes a carry-in port 10IN through which a printed circuit board W is carried in and a carry-out port 10OUT through which the printed circuit board W is carried out.

The stage 11 is a stage on which the printed circuit board W to be inspected is mounted and a conveyor mechanism is attached thereto. Specifically, the stage 11 is movable in a conveying direction (a direction from right to left in FIG. 1) along a predetermined horizontal direction and in a horizontal direction perpendicular to this conveying direction by a stage driver unit 11a. In the following description, a direction along the conveying direction of the stage 11 is referred to as an X direction; a horizontal direction perpendicular to the X direction as a Y direction; and a vertical direction as a Z direction (according to this definition, the stage 11 is driven along the X direction and Y direction by the stage driver unit 11a). The stage 11 conveys the printed circuit board W carried into the housing 10 through the carry-in port 10IN in the X direction up to a predetermined inspection position, stops and holds the printed circuit board W at the inspection position, and conveys the inspected printed circuit board W from the inspection position to the carry-out port 10OUT in the X direction.

A carry-in conveyor 12 for carrying the printed circuit board W into the stage 11 in the housing 10 is provided upstream of the stage 11 in the X direction in such a manner that a downstream end thereof faces the carry-in port 10IN. Further, a carry-out conveyor 14 for carrying out the printed circuit board W from the stage 11 to the outside of the housing 10 is provided downstream of the stage 11 in the X direction in such a manner that an upstream end thereof faces the carry-out port 10OUT. The carry-in conveyor 12 conveys printed circuit boards W finished with a predetermined step one by one onto the stage 11. The carry-out conveyor 14 carries out the printed circuit boards W finished with the inspection process in the X-ray inspection device A from the stage 11. These carry-in and carry-out conveyors 12, 14 are driven by conveyor driver units 12a, 14a and convey the printed circuit boards W at predetermined timings.

The X-ray radiation device 20 radiates X-rays to the printed circuit board W on the stage 11 in the housing 10. The X-ray camera 21 detects the X-rays radiated from the X-ray radiation device 20 and transmitted through the printed circuit board W (solder portions 101). That is, the X-ray camera 21 images an X-ray image of the printed circuit board W. The control unit 30 controls an imaging operation of the X-ray image by the X-ray radiation device 20 and the X-ray camera 21, an image processing operation for the obtained X-ray image and a quality determination operation of the solder portions 101. The display unit 40 displays the X-ray image processed by the control unit 30. Each of the above components is described in detail below.

The X-ray radiation device 20 is an X-ray source capable of radiating X-rays having high parallelism and includes a light emitter for generating X-rays and a collimator formed such that a plurality of thin tubes for transmitting X-rays are filled in a tube body. X-rays generated by the light emitter are incident on one end of the collimator and radiated from the other end of the collimator through the thin tubes. The X-ray radiation device 20 is carried movably only in the Z direction (vertical direction) substantially in a central part in the housing 10 by an X-ray radiation device driver unit 20a. The X-rays generated by the X-ray radiation device 20 are radiated to the printed circuit board W on the stage 11 from above the stage 11. The X-rays radiated from the X-ray radiation device 20 are transmitted through the printed circuit board W in an attenuated state by being partly absorbed by the printed circuit board W and the like.

The X-ray camera 21 is arranged to face the X-ray radiation device 20 across the printed circuit board W on the stage 11 and obtains an X-ray image of the printed circuit board W by detecting the X-rays transmitted through the printed circuit board W. For example, a panel with a light receiving surface having each side of 50 mm may be used as the X-ray camera 21. In such a case, the X-ray camera 21 is arranged about 15 cm below the stage 11. The X-ray camera 21 is movably carried in the housing 10 by an X-ray camera driver unit 21a and receives the X-rays transmitted through the printed circuit board W below the stage 11. The X-ray camera driver unit 21a displaces the X-ray camera 21 in the X and Y directions in accordance with an X-ray radiation direction by the X-ray radiation device 20. The X-ray camera 21 outputs data of the imaged X-ray image to the control unit 30.

The control unit 30 includes a CPU (Central Processing Unit) for performing a logical operation, a ROM (Read Only Memory) for storing a program and the like for controlling the CPU, a RAM (Random Access Memory) for temporarily storing various data during the operation of the device, an input/output interface and the like and is functionally provided with a stage controller 31, a conveyor controller 32, an imaging controller 33, an image processor 34, a quality determination processor 35, a program switching processor 36, a display controller 37 and an overall controller 30A. Further, an external storage device 50 (storage) for storing programs and various data (parameters) is connected to the input/output interface of the control unit 30.

The stage controller 31 is a module for controlling the operation of the stage 11 via the stage driver unit 11a singly or in conjunction with other controller(s). The conveyor controller 32 is a module for controlling the operation of the carry-in conveyor 12 and the carry-out conveyor 14 via the conveyor driver unit 12a, 14a singly or in conjunction with other controller(s). An operation of carrying the printed circuit board W into the housing 10 (onto the stage 11), an operation of moving and positioning the printed circuit board W on the stage 11 during X-ray imaging and an operation of carrying out the printed circuit board W after imaging are controlled by the above stage controller 31 and conveyor controller 32.

The imaging controller 33 is a module for controlling an operation of imaging an X-ray image by the X-ray radiation device 20 and the X-ray radiation camera 21 by driving the X-ray radiation device 20 and the X-ray radiation camera 21 via the X-ray radiation device driver unit 20a and the X-ray radiation camera driver unit 21a. Specifically, the imaging controller 33 adjusts the position of the X-ray radiation device 20 in the Z direction by the X-ray radiation device driver unit 20a and adjusts the position of the X-ray radiation camera 21 in an XY plane by the X-ray radiation camera driver unit 21a, thereby determining an X-ray transmission direction for the printed circuit board W (solder portions 101), i.e. an imaging direction and an elevation angle θ of the X-rays. Besides, the imaging controller 33 also controls a focus position of the X-rays radiated by the X-ray radiation device 20, an X-ray radiation amount, the number of times of imaging, an imaging timing and the like.

The image processor 34 is a module for processing data of an X-ray image imaged by the X-ray radiation camera 21, converting it into a predetermined image format and using the converted data in the application of a program handling such data. This image processor 34 is functionally provided with a thickness data computer 341, a cross-section graph generator 342 and a data synthesizer 343.

The thickness data computer 341 performs a process of converting luminance values of an X-ray image imaged by the X-ray camera 21 into thickness data. A main component of solder is tin (Sn). A relationship of Sn thickness and darkness (luminance) of an X-ray image, i.e. a relationship between Sn thickness and X-ray absorption amount can be easily grasped. Accordingly, the relationship of both can be formatted into a table in advance. In this embodiment, this table is stored in a conversion data storage 51 of the storage device 50 to be described later. The thickness data computer 341 computes thickness data by converting luminance values of the obtained X-ray image into thicknesses based on the table in the conversion data storage 51.

The cross-section graph generator 342 generates diagonal bar graph data corresponding to the cross-section data of the solder portion 101 based on the thickness data obtained by the thickness data computer 341. This diagonal bar graph data is obtained by inclining a bar chart indicating a thickness value of each part of a cross-section based on the thickness data according to the imaging direction and the imaging elevation angle of the printed circuit board W. Further, the cross-section graph generator 342 generates two pieces of diagonal bar graph data, i.e. data based on a bottom surface side of the solder portion 101 and data based on a top surface side of the solder portion 101. The cross-section graph generator 342 generates the above diagonal bar graph data based on the bottom surface side and the top surface side, i.e. two pieces of cross-section data for each of at least two X-ray images having different imaging directions.

The data synthesizer 343 extracts cross-section data of a part including a highly reliable region (described in detail later based on FIGS. 5 to 7) determined by the imaging direction of the printed circuit board W from a plurality of pieces of cross-section data generated by the cross-section graph generator 342. Then, the data synthesizer 343 synthesizes the extracted pieces of partial cross-section data to generate the entire cross-section data of the solder portion 101.

The quality determination processor 35 determines whether each solder portion 101 imaged is a good product (having a cross-section as shown in FIG. 4B) or a defective product (having, for example, a cross-section shown in FIG. 4C) by comparing the entire cross-section data of the solder portion 101 generated by the image processor 34 and a template or the like of the solder portion 101 as a basis for a good product.

The program switching processor 36 performs a process of switching a discrimination program prepared for each inspection target for quality determination of a cross-sectional shape. If the type of the printed circuit board W or the BGA 100 (type of an electronic component) to be inspected differs, controls, set parameters and the like may also differ. Thus, a plurality of types of discrimination programs need to be prepared according to inspection targets. In this embodiment, a plurality of types of discrimination programs are stored in a discrimination program storage 52 of the storage device 50 to be described later. The program switching processor 36 performs a process of reading the discrimination program corresponding to an inspection target from the discrimination program storage 52 and setting it as a work program when an input specifying the inspection target is given to an unillustrated operation unit from a user.

The display controller 37 executes a control for causing the display unit 40 to display data handled by the control unit 30 by a GUI (Graphical User Interface) based on the program.

The overall controller 30A is a module for totally controlling the operation of the X-ray inspection device A and executes a control for causing the aforementioned stage controller 31, conveyor controller 32, imaging controller 33, image processor 34, quality determination processor 35, program switching processor 36 and display controller 37 to operate at predetermined timings based on a predetermined program sequence.

The display unit 40 is composed of a liquid crystal display and the like and displays a necessary screen based on the control of the control unit 30 (display controller 37). For example, the display unit 40 displays X-ray images obtained by the X-ray camera 21, cross-section data to be described later and the like.

The storage device 50 is a device for storing various data and programs used for the X-ray inspection device A and, in this embodiment, include the conversion data storage 51, the discrimination program storage 52 and a facility specific data storage 53.

A table indicating a relationship between the thickness of Sn as a main constituent material of the solder portions 101 and a luminance value when X-rays are transmitted is stored in the conversion data storage 51. This table is a table using the Sn thickness and the X-ray transmission amount when a predetermined amount of X-rays are radiated to Sn members having different thicknesses as parameters, and is obtained by actual measurement or simulation. A plurality of types of discrimination programs prepared in advance according to inspection targets are stored in the discrimination program storage 52. Dimension data, various set data and the like of each constituent element of the X-ray inspection device A are stored in the facility specific data storage 53.

Figure 5:
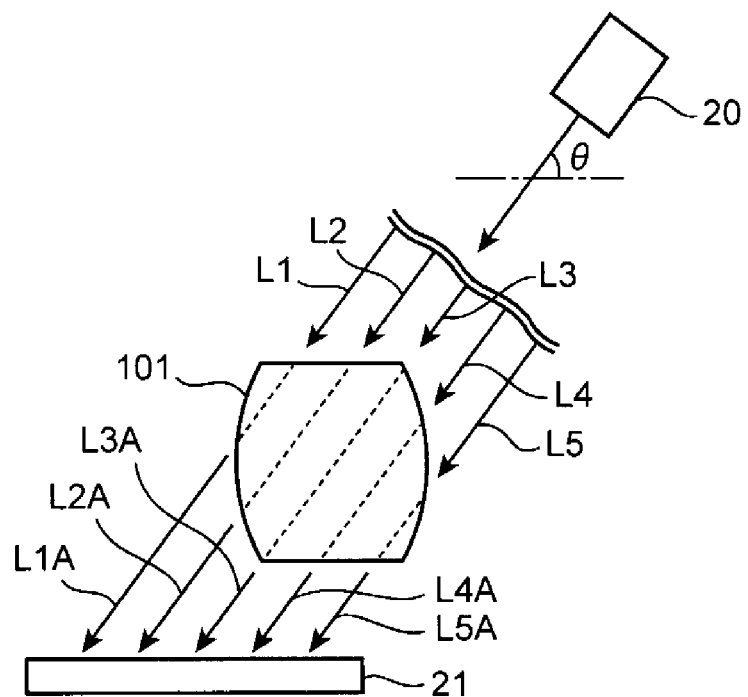
FIG. 5 is a diagram showing a state of irradiation of X-rays to an inspection target.

Next, the highly reliable region in the X-ray image data (cross-section data) is described based on FIGS. 5 to 7. FIG. 5 is a diagram showing a state of irradiation of X-rays to the solder portion 101 as an inspection target and FIGS. 6 and 7 are diagrams showing highly reliable regions of an X-ray image in the case of radiation of X-rays to the solder portion 101 in a first direction and a second direction.

With reference to FIG. 5, it is assumed that the X-ray radiation device 20 is arranged at a predetermined elevation angle θ (e.g. θ=45°) in a predetermined direction above the solder portion 101 as an inspection target. Collimated X-rays L1 to L5 are radiated from the X-ray radiation device 20 and incident on the solder portion 101 having a barrel shape in a side view. The X-rays L1 to L5 are transmitted through the solder portion 101 obliquely from a right upper side to a left lower side of the solder portion 101. Transmitted X-rays L1A to L5A of the X-rays L1 to L5 are incident on a light receiving surface of the X-ray camera 21.

Here, if transmission lengths of the respective X-rays L1 to L5 through the solder portion 101 are compared, the X-ray L3 transmitted near a diagonal of the barrel-shaped solder portion 101 has a longest transmission length and the X-rays L2, L4 adjacent to this also have relatively long transmission lengths. Contrary to this, the X-ray L1 transmitted near a left upper end of the solder portion 101 and the X-ray L5 transmitted near a right lower end of the solder portion 101 have short transmission lengths. As the transmission length through the solder portion 101 mainly containing Sn increases, an attenuation amount of the X-ray increases. Accordingly, the transmitted X-ray L3A has a smallest light amount and the transmitted X-rays L2A and L4A also have relatively small light amounts. On the other hand, the transmitted X-rays L1A and L5A have relatively large light amounts. Thus, the X-ray image imaged by the X-ray camera 21 is darkest (low luminance value) near a region where the transmitted X-ray L3A is incident and also considerably dark near regions where the transmitted X-rays L2A and L4A are incident while being relatively bright (high luminance value) near regions where the transmitted X-rays L1A and L5A are incident.

A black region where the luminance values are low has a poor thickness resolution. This is because it is difficult to observe differences among the luminance values in the black region. For example, the vicinity of the region where the transmitted X-ray L3A of the X-ray image is incident and the vicinities of the regions where the transmitted X-rays L2A and L4A are incident are black image regions where luminance differences are hardly recognized. Accordingly, the reliability of thickness data obtained by converting the luminance values of these regions into thicknesses is low no matter what. Contrary to this, since changes in the luminance value corresponding to the thickness of the solder portion 101 can be observed near the regions where the transmitted X-rays L1A and L5A are incident, the reliability of thickness data obtained by converting the luminance values in these regions into thicknesses is high.

Figure 6A:
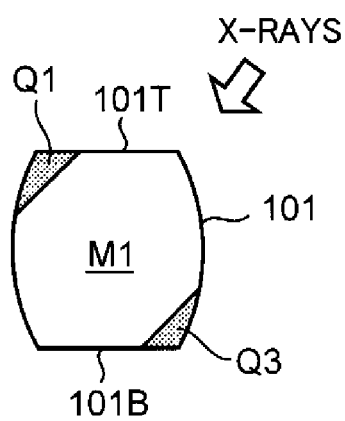
Figure 6B:
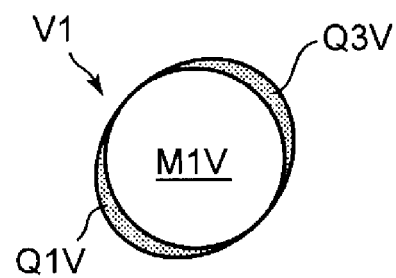

FIGS. 6A and 6B are diagrams showing highly reliable regions of an X-ray image when X-rays are radiated to the solder portion 101 obliquely from a right upper side of the solder portion 101 (in a first direction), wherein FIG. 6A is a side view of the solder portion 101 and FIG. 6B shows an X-ray image V1 of the solder portion 101. In this case, the vicinity of a left end part on the side of a top surface 101T of the solder portion 101 is an edge region Q1 having a short X-ray transmission length and the vicinity of a right end part on the side of a bottom surface 101B is also an edge region Q3 having a short X-ray transmission length. On the other hand, a part between the edge regions Q1 and Q3 is an intermediate region M1 having a long X-ray transmission length. Accordingly, in the X-ray image V1, image regions Q1V, Q3V corresponding to the edge regions Q1, Q3 are highly reliable regions and an image region M1V corresponding to the intermediate region M1 is a region having relatively low reliability.

Figure 7A:
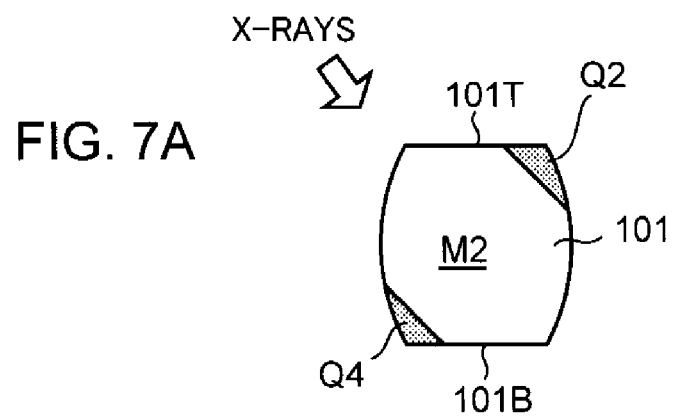
Figure 7B:
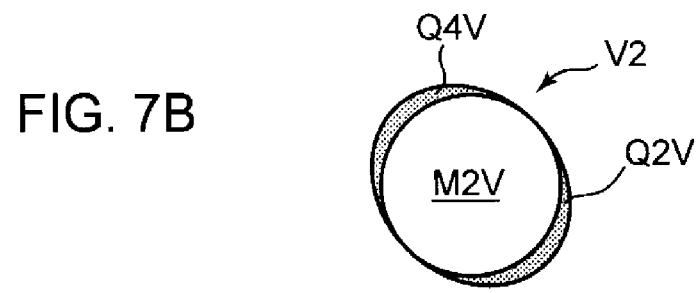

FIGS. 7A and 7B are diagrams showing highly reliable regions of an X-ray image when X-rays are radiated to the solder portion 101 in a direction different by 180° from FIGS. 6A and 6B, i.e. obliquely from a left upper side of the solder portion 101 (in a second direction), wherein FIG. 7A is a side view of the solder portion 101 and FIG. 7B shows an X-ray image V2 of the solder portion 101. In this case, the vicinity of a right end part on the side of the top surface 101T of the solder portion 101 is an edge region Q2 having a short X-ray transmission length and the vicinity of a left end part on the side of the bottom surface 101B is also an edge region Q4 having a short X-ray transmission length. On the other hand, a part between the edge regions Q2 and Q4 is an intermediate region M2 having a long X-ray transmission length. Accordingly, in the X-ray image V2, image regions Q2V, Q4V corresponding to the edge regions Q2, Q4 are highly reliable regions and an image region M2V corresponding to the intermediate region M2 is a region having relatively low reliability.

As described above, the highly reliable regions of the X-ray image are determined by the arrangement position of the X-ray radiation device 20 with respect to the solder portion 101, i.e. the imaging direction of the solder portion 101 by the X-ray camera 21. If parts including the image regions Q1V to Q4V of the highly reliable regions are extracted from the X-ray images V1, V2 and are synthesized to derive one piece of cross-section data of the solder portion 101, it is possible to obtain a highly reliable vertical cross-sectional shape of the solder portion 101. In addition, the solder portion 101 has a barrel shape and is one of rotationally symmetrical three-dimensional shapes. Thus, the vertical cross-sectional shape of the solder portion 101 can be obtained if the solder portion 101 is X-ray imaged at least in two directions.

First Example of Deriving Cross-Section Data

Figure 8C:
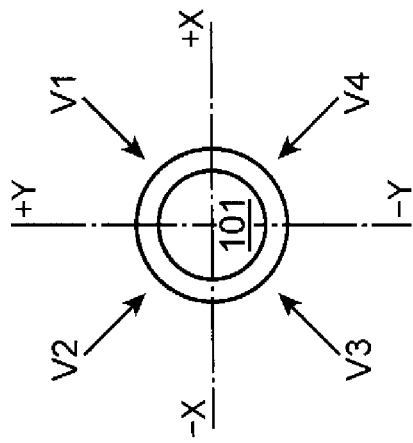
FIGS. 8A and 8B are a perspective view and a side view showing an inspection target and FIG. 8C is a plan view showing imaging directions.
Figure 8B:
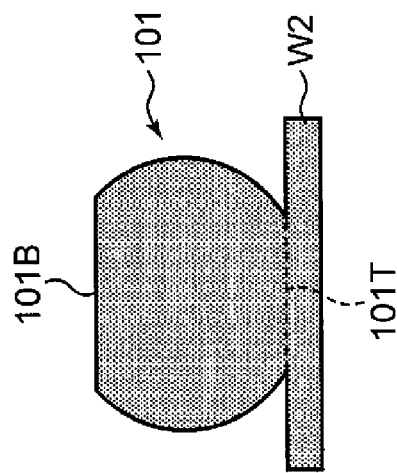
Figure 8A:
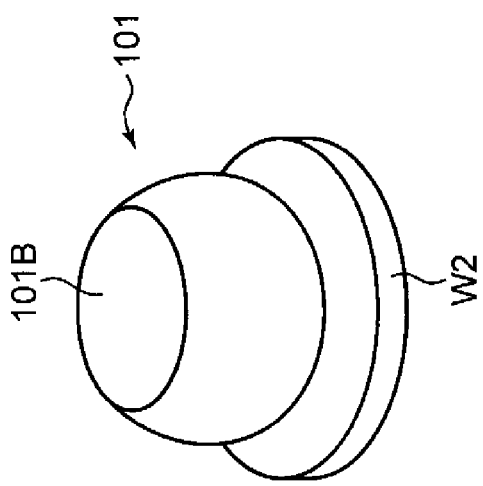

Next, a method for deriving the cross-section data of the solder portion 101 is specifically described. FIG. 8A is a perspective view of the solder portion 101 as an inspection target, FIG. 8B is a side view thereof and FIG. 8C is a plan view showing X-ray imaging directions of the solder portion 101. As described above and also shown in FIGS. 8A and 8B, the solder portion 101 has the barrel shape whose top surface 101T (first surface) and bottom surface 101B (second surface) are flat circular surfaces and whose side peripheral wall has an outwardly convex curved surface. Note that the electrode W2 of the BGA 100 and a part corresponding to the solder ball 103 are shown upside down.

As shown in FIG. 8C, there are four imaging directions of the solder portion 101 spaced apart at equal angles in a plan view. Specifically, the X-ray imaging of the solder portion 101 is conducted in four directions spaced apart from each other at an angle of 90°, i.e. a 45° direction V1, a 135° direction V2, a 225° direction V3 and a 315° direction V4 counterclockwise from an +X axis as an origin axis. Further, an imaging elevation angle is 45° in any case. For example, in imaging in the 45° direction V1, the imaging controller 33 (see FIG. 2) causes the X-ray radiation device 20 to be arranged in the 315° direction and the X-ray camera 21 to be arranged in the 45° direction and, in this state, causes the X-ray radiation device 20 to radiate X-rays and causes the X-ray camera 21 to obtain an X-ray image. Of course, imaging may be performed in more than four directions and, for example, may be performed in eight directions spaced apart at an angle of 45° from each other. Alternatively, imaging may be performed in directions that are not spaced at equal angles. Further, although the elevation angles are preferably equal, imaging may be performed at different elevation angles.

Note that an X-ray image in a direction vertical to the solder portion 101 is also obtained in addition to those obtained in the above four or eight directions. This is to obtain length data from the top surface 101T to the bottom surface 101B of the solder portion 101. In this case, an imaging operation is performed with the X-ray radiation device 20 arranged to face the top surface 101T of the solder portion 101 and the X-ray camera 21 arranged to face the bottom surface 101B. The imaging controller 33 controls the X-ray radiation device 20 and the X-ray camera 21 via the X-ray radiation device driver unit 20a and the X-ray camera driver unit 21a so as to perform the above imaging.

Figure 9:
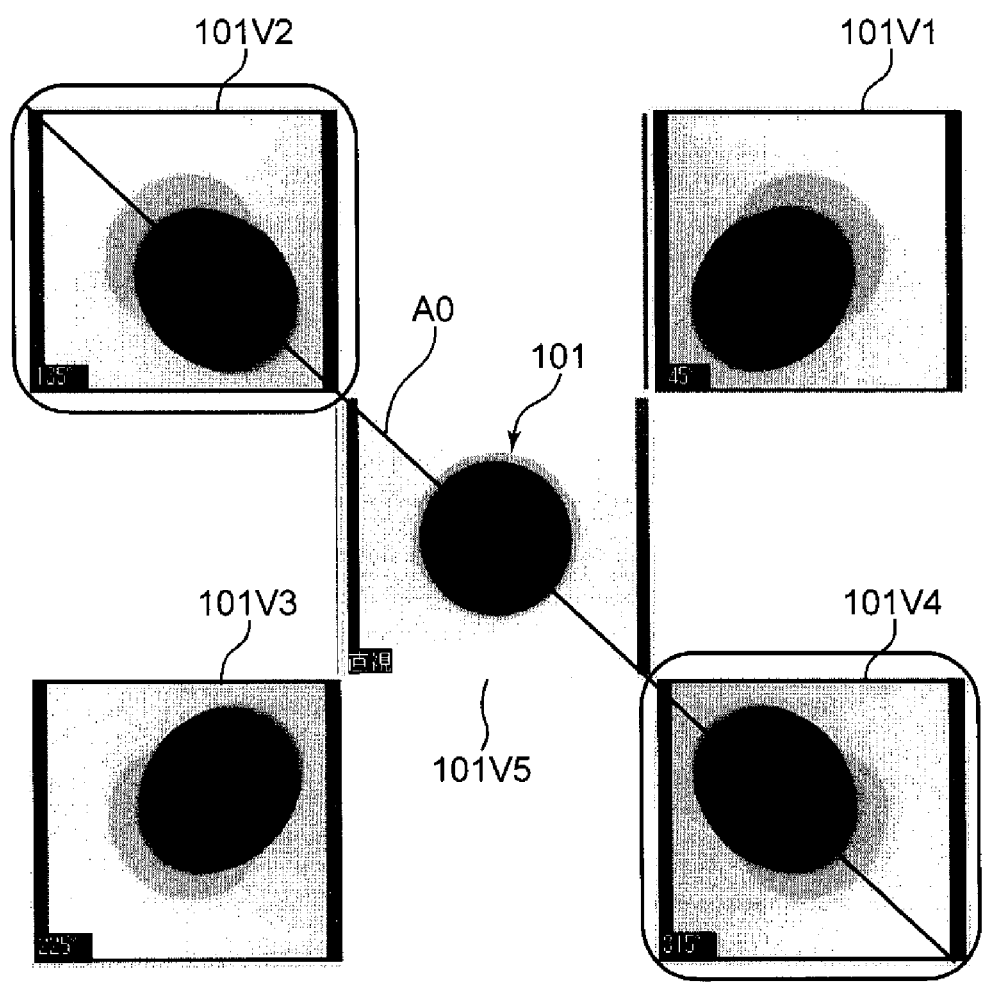
FIG. 9 is a view showing an arrangement of X-ray images of the inspection target obtained in the respective imaging directions.

FIG. 9 is a view showing an array of X-ray images 101V1 (45° direction V1), 101V2 (135° V2), 101V3 (225° direction V3), 101V4 (315° direction) and 101V5 (vertical direction) of the solder portion 101 obtained in the four imaging directions and the vertical imaging direction shown in FIG. 8C according to the imaging directions. Out of these X-ray images, the X-ray image 101V2 (hereinafter, referred to as a first X-ray image VD1) in the 135° direction V2 (first direction) and the X-ray image 101V4 (hereinafter, referred to as a second X-ray image VD2) in the 315° direction V4 (second direction), both being located on a straight line A0, are used. If the X-ray images in two directions facing each other (first and second directions) and having the same elevation angle (first and second elevation angles) are used in this way, cross-section data along one cross-section line A0 can be obtained. Further, since the elevation angles in both directions are equal, a synthesis process of the cross-section data of the highly reliable regions can be simplified. Note that the X-ray image 101V5 in the vertical direction (hereinafter, referred to as a third X-ray image VD3) is also used to obtain the above length data.

Next, a process in the image processor 34 is described in detail. First, the thickness data computer 341 of the image processor 34 computes a luminance value distribution of a cross-section along the straight line A0 of FIG. 9 (along the first or second direction) for each of the obtained first, second and third X-ray images VD1, VD2 and VD3. Further, the thickness data computer 341 converts the luminance values into thicknesses based on the conversion table of the luminance values and the Sn thicknesses stored in the conversion data storage 51, whereby first thickness data, second thickness data and third thickness data of the A0 cross-section are computed for the first, second and third X-ray images VD1, VD2 and VD3.

Subsequently, by the cross-section graph generator 342, diagonal bar graph data equivalent to the cross-section data of the solder portion 101 is generated based on the first and second thickness data computed by the thickness data computer 341. Two pieces of this diagonal bar graph data (cross-section data) are prepared for each piece of thickness data based on the top surface 101T side (first surface side) and the bottom surface 101B side (second surface side) of the solder portion 101.

Figure 10:
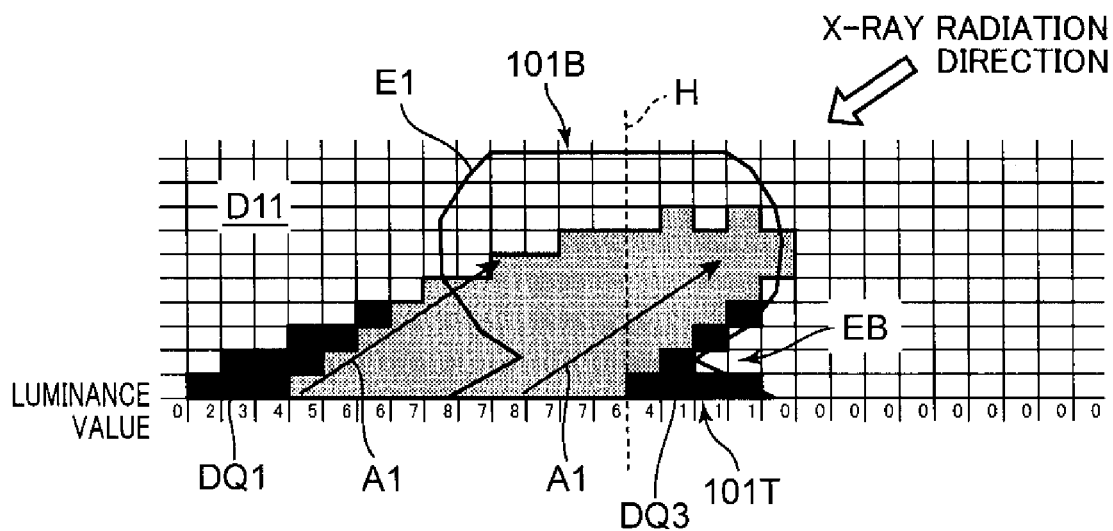
FIG. 10 is a diagonal bar graph showing an example of cross-section data.

FIG. 10 is a graph showing cross-section data D11 (first cross-section data) developed based on the top surface 101T side for the first thickness data. This cross-section data D11 is obtained by dividing the straight line A0 into blocks having a predetermined width and obliquely inclining a bar graph (bars become taller with approach toward black) of the thickness data converted from the luminance values by the block along an arrow A1 corresponding to the imaging direction and the elevation angle (135° direction, elevation angle of 45°). A numerical value shown as the "luminance value" on a horizontal axis corresponds to the height of a diagonal bar having the corresponding block as a base. For example, in the block to which a numeral value of 5=luminance value is given, a stacked height of unit grids is five with the grid directly above the numerical value 5 as a base when viewed in a direction of the arrow A1. That is, the larger (darker) the luminance value, the longer the X-ray transmission length and the longer the diagonal bar. Note that, as described based on FIGS. 5 to 7, the longer the X-ray transmission length, the lower the reliability of the thickness data.

The cross-section data D11 is cross-section data obtained from the X-ray image imaged in the imaging direction described in FIG. 6. Thus, in the cross-section data D11, groups of grids on opposite sides shown by a dark color in FIG. 10 are equivalent to the edge regions Q1, Q3 having short X-ray transmission lengths, and these grid groups serve as highly reliable region data DQ1, DQ3. Of course, the diagonal bars to which these pieces of highly reliable region data DQ1, DQ3 belong have small luminance values. On the other hand, a grid group in an intermediate part shown by a light color in FIG. 10 is equivalent to the intermediate region M1 having a long X-ray transmission length and the diagonal bars belonging to this region have large luminance values.

Figure 11:
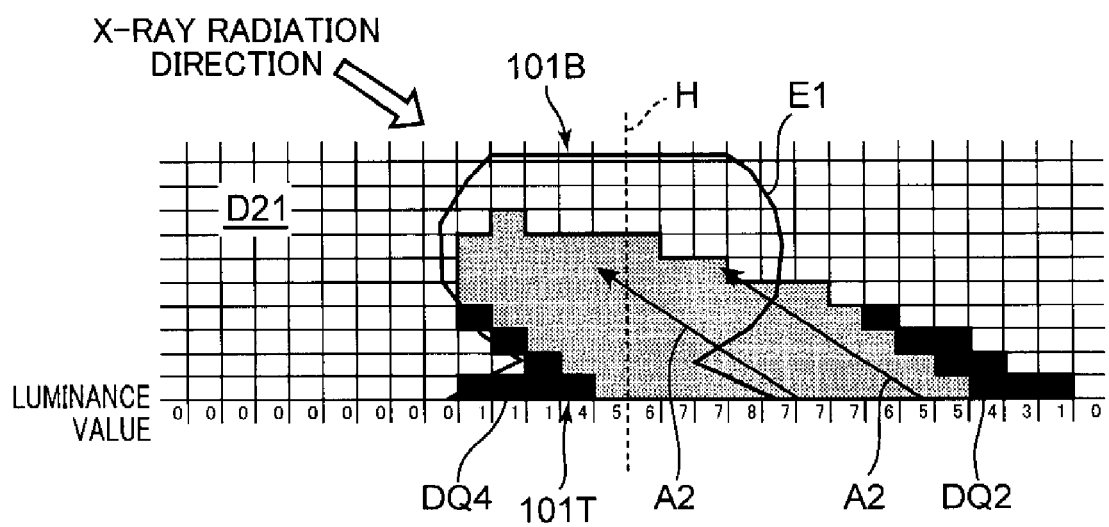
FIG. 11 is a diagonal bar graph showing an example of cross-section data.

Note that a cross-sectional silhouette E1 of the solder portion 101 as a target is shown in FIGS. 10 and 11 to be described next. This silhouette E1 is a cross-sectional silhouette not of a barrel-shaped good product, but of a defective product having a small-diameter portion EB near the top surface 101T. Since X-rays are radiated obliquely from the right upper side as shown by a void arrow in FIG. 10 to obtain the cross-section data D11, the highly reliable region data DQ3 is data corresponding to an actual image near the top surface 101T of the solder portion 101. On the other hand, the highly reliable region data DQ1 is data corresponding to a projected image of the solder portion 101 and does not reflect an actual shape of the solder portion 101. Accordingly, in the cross-section data D11, the highly reliable region data DQ3 and data near it are data with high usability. If the cross-section data D11 is simply divided, data in a right half of the silhouette E1 to the right of a vertical center line H is data with high usability.

FIG. 11 is a graph showing cross-section data D21 (third cross-section data) developed based on the top surface 101T side for the second thickness data. This cross-section data D21 is obtained by dividing the straight line A0 into blocks having a predetermined width and obliquely inclining a bar graph of the thickness data converted from the luminance values by the block along an arrow A2 corresponding to the imaging direction and the elevation angle (315° direction, elevation angle of 45°). The cross-section data D21 is cross-section data obtained from the X-ray image imaged in the imaging direction described in FIGS. 7A and 7B. Thus, in the cross-section data D21, groups of grids on opposite sides shown by a dark color in FIG. 11 are equivalent to the edge regions Q2, Q4 having short X-ray transmission lengths, and these grid groups serve as the highly reliable region data DQ2, DQ4.

Since X-rays are radiated obliquely from the left upper side to obtain the cross-section data D21, the highly reliable region data DQ4 is data corresponding to an actual image near the top surface 101T of the solder portion 101. On the other hand, the highly reliable region data DQ2 is data corresponding to a projected image of the solder portion 101 and does not reflect an actual shape of the solder portion 101. Accordingly, in the cross-section data D21, the highly reliable region data DQ4 and data near it are data with high usability. If the cross-section data D21 is simply divided, data in a left half of the silhouette E1 to the left of a vertical center line H is data with high usability.

Figure 12A:
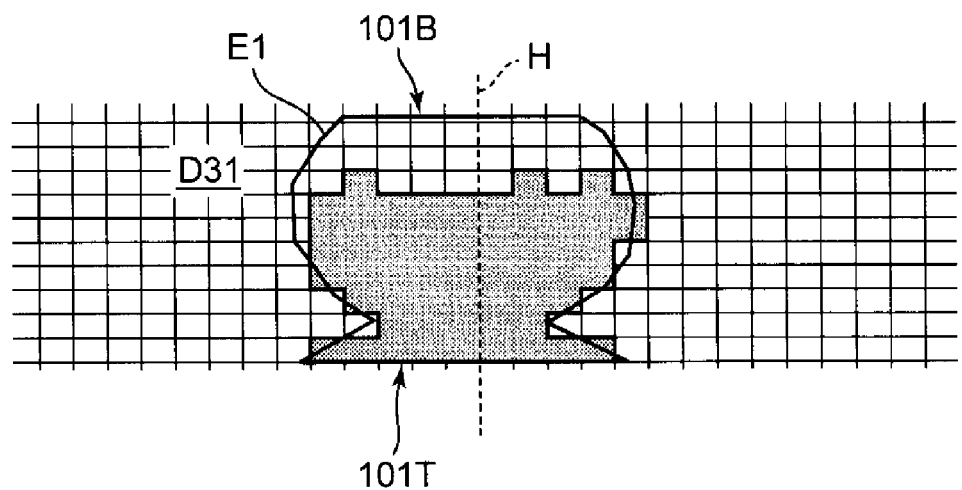
FIGS. 12A and 12B are graphs showing a synthesis example of the cross-section data of FIG. 10 and that of FIG. 11.
Figure 12B:
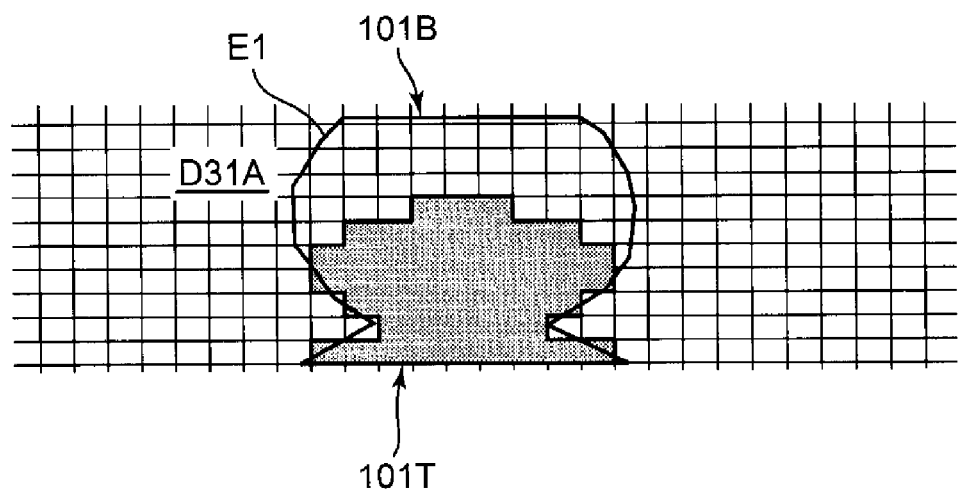

The above cross-section data D11 and cross-section data D21 are synthesized by the data synthesizer 343. FIGS. 12A and 12B are graphs showing a synthesis example of two pieces of data by the data synthesizer 343. FIG. 12A shows cross-section data D31 obtained by a synthesis technique of extracting right half data to the right of the center line H of the silhouette E1 from the cross-section data D11, extracting left half data to the left of the center line H from the cross-section data D21 and joining these pieces of partial cross-section data at the edge of the center line H. FIG. 12B shows cross-section data D31A obtained by a synthesis technique of overlapping the cross-section data D11 and the cross-section data D21 and, if one of the grids of the overlapped both pieces of data is a "white grid", treating this grid as the "white grid" (i.e. treating that no shape is present).

By both the synthesis techniques of FIGS. 12A and 12B, the highly reliable region data DQ3 with high usability and data near it are extracted from the cross-section data D11 and the highly reliable region data DQ4 with high usability and data near it are extracted from the cross-section data D21 to generate the synthesized cross-section data D31 or D31A. Thus, the cross-section data D31 or D31A is cross-section data precisely representing a cross-sectional shape of the vicinity of the top surface 101T of the solder portion 101.

Next, the cross-section graph generator 342 generates diagonal bar graph data (cross-section data) based on the bottom surface 101B side of the solder portion 101 respectively based on the first thickness data and the second thickness data obtained by the thickness data computer 341. These pieces of cross-section data can be generated by reconfiguring the cross-section data D11 and the cross-section data D21, which are generated first based on the top surface 101T side, to be based on the bottom surface 101B side.

Figure 13:
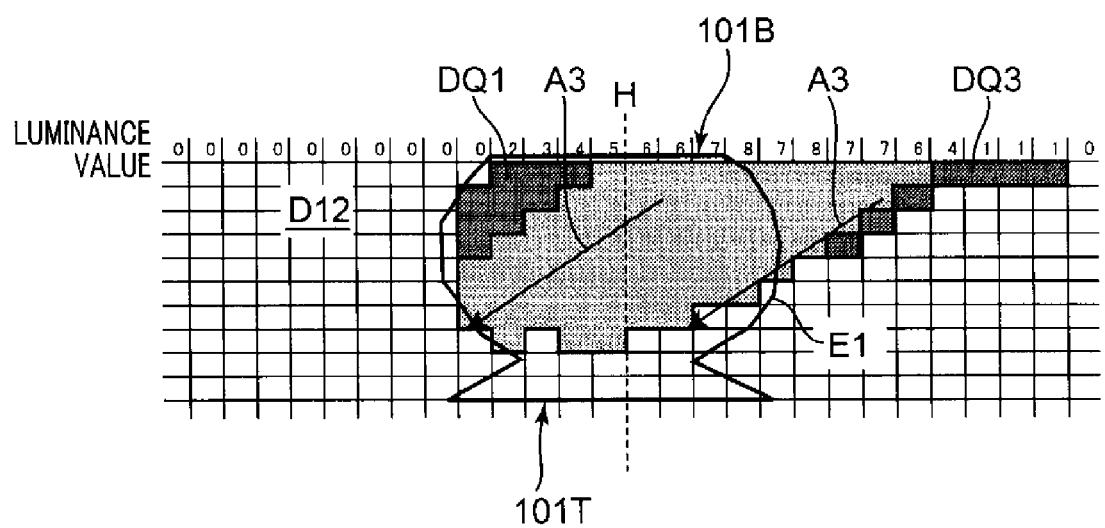
FIG. 13 is a diagonal bar graph showing an example of cross-section data.

FIG. 13 is a graph showing cross-section data D12 (second cross-section data) developed based on the bottom surface 101B side for the first thickness data. In the cross-section data D12, numerical values shown as the "luminance values" on a horizontal axis on the bottom surface 101B side are the same as the numerical values shown as the "luminance values" on the horizontal axis on the top surface 101T side in FIG. 10 described above. Data obtained by reconfiguring a bar graph of thickness data converted from this "luminance values" such that the bar graph obliquely hangs down along an arrow A3 in a direction directly opposite to the arrow A1 of FIG. 10 from the bottom surface 101B side is the cross-section data D12.

In the cross-section data D12 thus reconfigured, the highly reliable region data DQ1 is data corresponding to an actual image of the vicinity of the bottom surface 101B of the solder portion 101 contrary to FIG. 10. That is, the highly reliable region data DQ1 and data near it serve as data with high usability. If the cross-section data D12 is simply divided, data in a left half of the silhouette E1 to the left of the vertical center line H is data with high usability.

Figure 14:
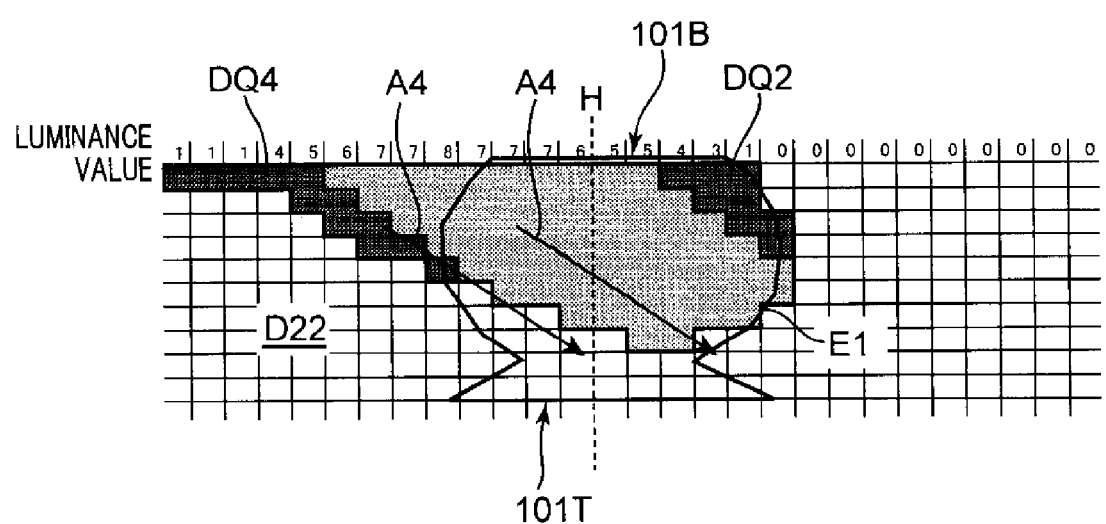
FIG. 14 is a diagonal bar graph showing an example of cross-section data.

Similarly, FIG. 14 is a graph showing cross-section data D22 (fourth cross-section data) developed based on the bottom surface 101B side for the second thickness data. Also in this cross-section data D22, numerical values shown as the "luminance values" on a horizontal axis on the bottom surface 101B side are the same as the numerical values shown as the "luminance values" on the horizontal axis on the top surface 101T side in FIG. 11. Data obtained by reconfiguring a bar graph of thickness data converted from the "luminance values" such that the bar graph obliquely hangs down along an arrow A4 in a direction directly opposite to the arrow A2 of FIG. 11 from the bottom surface 101B side is the cross-section data D22.

In the cross-section data D22 thus reconfigured, the highly reliable region data DQ2 is data corresponding to an actual image of the vicinity of the bottom surface 101B of the solder portion 101 contrary to FIG. 11. That is, the highly reliable region data DQ2 and data near it serve as data with high usability. If the cross-section data D22 is simply divided, data in a right half of the silhouette E1 to the right of the vertical center line H is data with high usability.

Figure 15A:
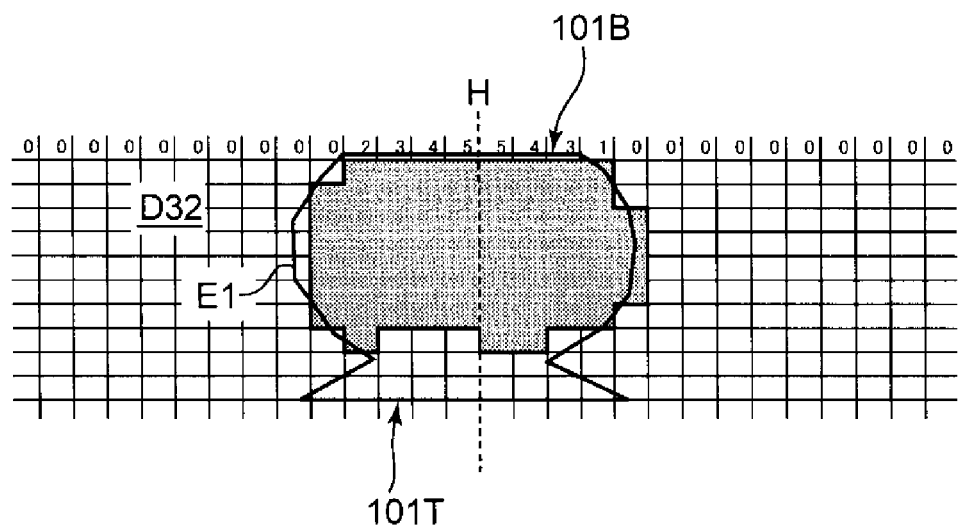
FIGS. 15A and 15B are graphs showing a synthesis example of the cross-section data of FIG. 13 and that of FIG. 14.
Figure 15B:
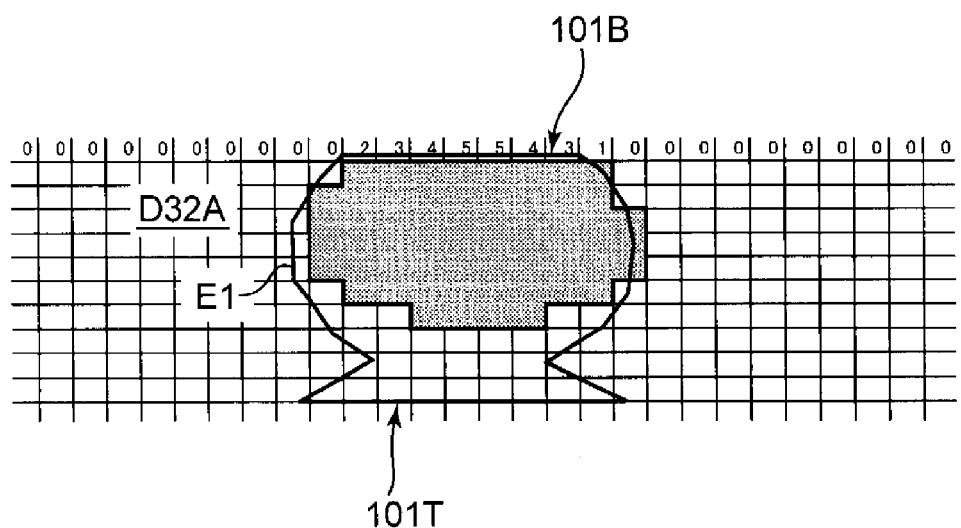

The above cross-section data D12 and cross-section data D22 are also synthesized by the data synthesizer 343. FIGS. 15A and 15B are graphs showing a synthesis example of two pieces of data by the data synthesizer 343. FIG. 15A shows cross-section data D32 obtained by a synthesis technique of extracting left half data to the left of the center line H of the silhouette E1 from the cross-section data D12, extracting right half data to the right of the center line H from the cross-section data D22 and joining these pieces of partial cross-section data at the edge of the center line H. FIG. 15B shows cross-section data D32A obtained by a synthesis technique of overlapping the cross-section data D12 and the cross-section data D22 and, if one of grids of the overlapped both pieces of data is a "white grid", treating this grid as the "white grid".

By both the synthesis techniques of FIGS. 15A and 15B, the highly reliable region data DQ1 with high usability and data near it are extracted from the cross-section data D12 and the highly reliable region data DQ2 with high usability and data near it are extracted from the cross-section data D22 to generate the synthesized cross-section data D32 or D32A. Thus, the cross-section data D32 or D32A is cross-section data precisely representing a cross-sectional shape of the vicinity of the bottom surface 101B of the solder portion 101.

Figure 16:
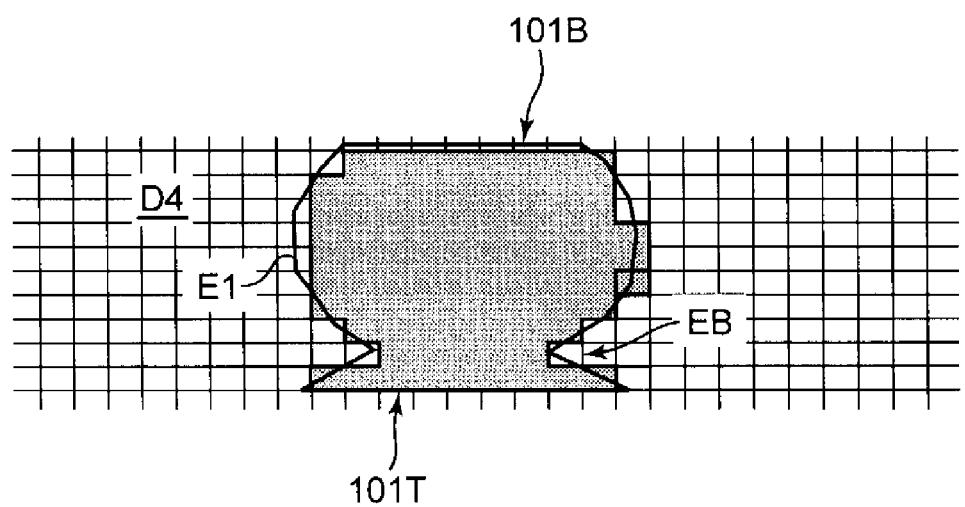
FIG. 16 is a graph showing a synthesis example of the cross-section data of FIG. 12 and that of FIG. 15.

The data synthesizer 343 further performs a process of synthesizing the aforementioned cross-section data D31 and D32 or cross-section data D31A and D32A. FIG. 16 is a graph showing synthesized cross-section data D4 obtained by synthesizing the cross-section data D31 and D32 or the cross-section data D31A and D32A. One of the synthesis techniques is a technique of extracting data corresponding to a substantially half of the top surface 101T side of the silhouette E1 from the cross-section data D31 or D31A, extracting data corresponding to a substantially half of the bottom surface 101B side of the silhouette E1 from the cross-section data D32 or D32A and synthesizing these pieces of extracted data. Another synthesis technique is a technique of overlapping the cross-section data D31 or D31A and the cross-section data D32 or D32A and, if one of the grids of the overlapped pieces of data is a "white grid", treating this grid as the "white grid". Of course, the synthesized cross-section data D4 may be synthesized from the cross-section data D11, D12, D21 and D22 by omitting the intermediate synthesis of the cross-section data D31 or D31A and the cross-section data D32 or D32A.

Here, length data from the top surface 101T to the bottom surface 101B of the solder portion 101 is necessary to synthesize the cross-section data D31 or D31A and the cross-section data D32 or D32A. This is because the cross-section data D11, D21 as a basis for the cross-section data D31, D31A is data depending only on the top surface 101T and the cross-section data D12, D22 as a basis for the cross-section data D32, D32A is data depending only on the bottom surface 101B. The data synthesizer 343 uses the third thickness data obtained from the third X-ray image VD3 obtained in the vertical direction to derive the length data. This third thickness data is data obtained by converting a luminance value distribution along the straight line A0 of the third X-ray image VD3 into thicknesses using the conversion table in the conversion data storage 51. Thus, the length data from the top surface 101T to the bottom surface 101B can be obtained from the third thickness data. The data synthesizer 343 defines coordinate positions of the top surface 101T and the bottom surface 101B according to the length data and performs a process of synthesizing the cross-section data D31 or D31A and the cross-section data D32 or D32A.

Since the synthesized cross-section data D4 obtained as described above is a synthesis of the highly reliable region data DQ1 to DQ4, it precisely represents a vertical cross-sectional shape of the solder portion 101. Actually, the synthesized cross-section data D4 coincides with the silhouette E1 having the small-diameter portion EB. The quality determination processor 35 compares the obtained synthesized cross-section data D4 and a reference silhouette of the solder portion 101 as a basis for a good product and determines whether or not the synthesized cross-section data D4 is a good product.

For example, the reference silhouette can be set by estimating a barrel shape of a good product from the total amount of solder of the solder portion 101, i.e. the total amount of solder used in one pair of a solder ball 103 and a solder 102, and sink information after the reflow process. The solder portion 101 as a good product has a rotationally symmetrical three-dimensional shape. That is, a vertical cross-section has the same barrel shape regardless of in which direction the solder portion 101 is cut. On the other hand, the solder portion 101 as a defective product does not have a barrel shape, for example, as in the silhouette E1. Thus, whether or not the solder portion 101 is a good product can be determined based on whether or not the synthesized cross-section data D4 represents a barrel shape.

The method for inspecting the vertical cross-sectional shape thereof is described above, taking one solder portion 101 as an example. In an actual inspection, X-ray images of a plurality of solder portions 101 are obtained by an imaging operation of one routine. Depending on the solder portion 101, another electronic component or the like mounted on the printed circuit board W may be reflected as an obstacle if the solder portion 101 is imaged in a certain imaging direction. As described above, the imaging controller 33 causes the printed circuit board W (solder portions 101) to be imaged in four directions spaced apart at an equal angular interval of 90° or in eight directions spaced apart at an equal angular interval of 45°. According to this embodiment, the cross-section data can be derived if X-ray images imaged in two different directions are available. Therefore, the above quality determination can be made by selecting a pair of imaging directions not influenced by obstacles out of all the imaging directions.

Second Example of Deriving Cross-Section Data

Figure 17:
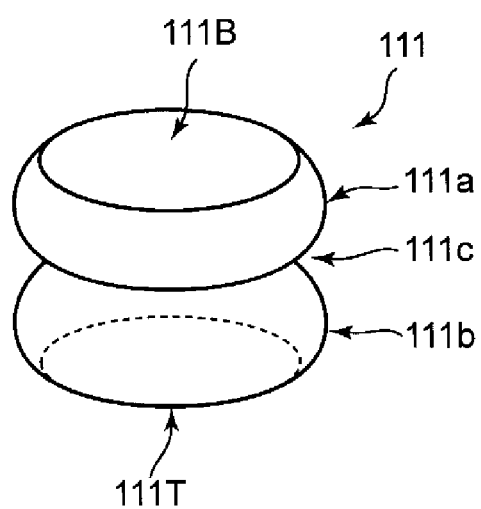
FIG. 17 is a perspective view of another inspection target.

FIG. 17 is a perspective view showing a target according to a second example of deriving cross-section data. This target is a solder portion 111 different from the first example and has a three-dimensional shape divided into a bottom surface part 111a located on a bottom surface 111B side and a top surface part 111b located on a top surface 111T side, the both parts being in contact at an intermediate part 111c. Of course, this solder portion 111 is also an example of a defective product. An example of obtaining a vertical cross-sectional shape of such a solder portion 111 is described.

Also in this second example, as shown in FIG. 9, vertical cross-section data along a straight line A0 is obtained using a first X-ray image obtained in the 135° direction (first direction) at an elevation angle of 45°, a second X-ray image obtained in the 315° direction (second direction) at an elevation angle of 45° and a third X-ray image obtained in the vertical direction. Similarly to the first example, the thickness data computer 341 of the image processor 34 first obtains first, second and third thickness data of an A0 cross-section for the first, second and third X-ray images based on the conversion table in the conversion data storage 51.

Subsequently, the cross-section graph generator 342 generates diagonal bar graph data corresponding to the cross-section data of the solder portion 111 based on the first and second thickness data. FIG. 18A is a graph showing cross-section data D51 (first cross-section data) developed based on the top surface 111T side for the first thickness data. FIG. 18B is a graph showing cross-section data D61 (third cross-section data) developed based on the top surface 111T side for the second thickness data. Further, FIG. 18C shows cross-section data D71 obtained by synthesizing the cross-section data D51 and D61 by the data synthesizer 343.

Figure 19A:
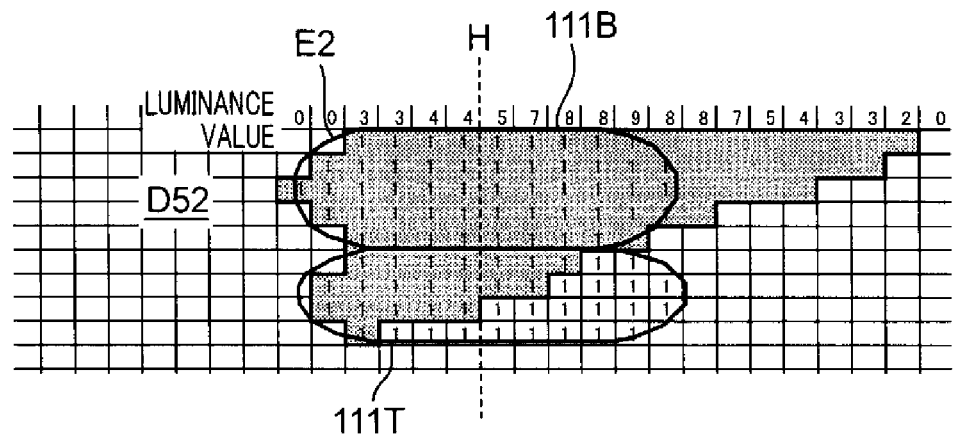
FIGS. 19A and 19B are diagonal bar graphs showing examples of cross-section data and FIG. 19C is a graph showing a synthesis example of these pieces of cross-section data.
Figure 19B:
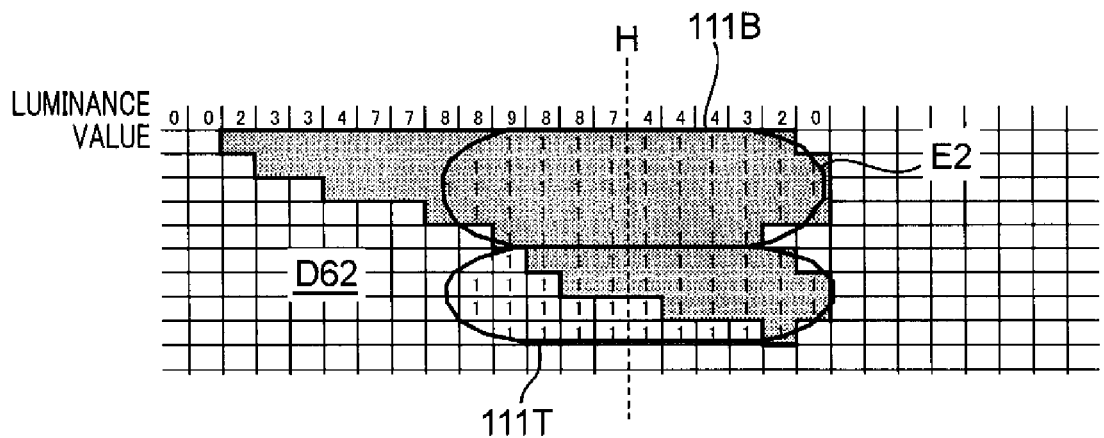
Figure 19C:
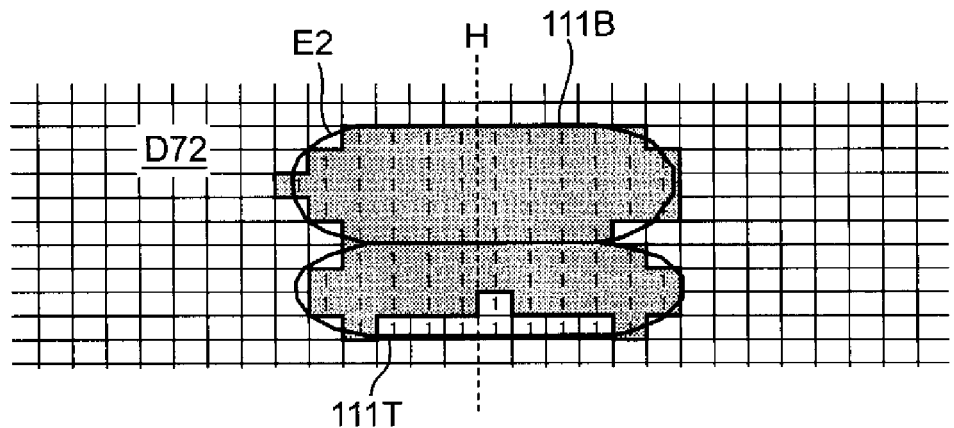
Figure 20:
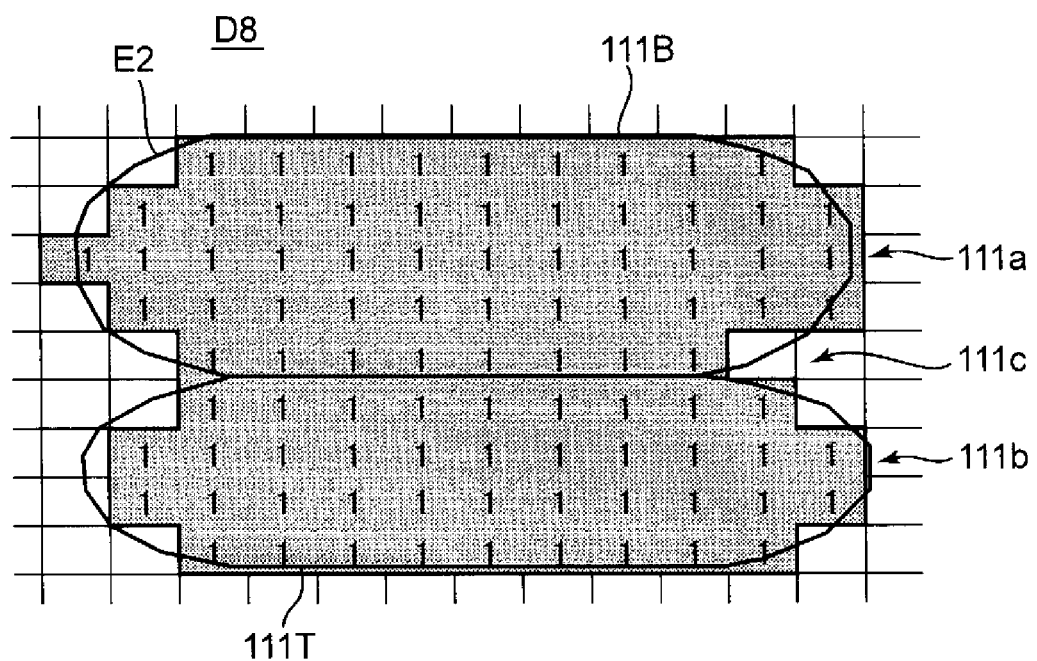
FIG. 20 is a graph showing a synthesis example of the cross-section data of FIG. 18C and that of FIG. 19C.

In FIG. 18 and FIGS. 19 and 20 described below, a silhouette E2 of the solder portion 111 is shown. Further, a numerical value of "1" given to each grid in the silhouette E2 indicates that this grid is a grid where an object is supposed to be present.

The cross-section data D51 of FIG. 18A is thickness data whose diagonal bars on a side to the right of a vertical center line H of the silhouette E2 and at a luminance value of 4 or smaller are highly reliable as described in detail in the previous first example. On the other hand, the cross-section data D61 of FIG. 18B is thickness data whose diagonal bars on a side to the left of the vertical center line H of the silhouette E2 and at a luminance value of 4 or smaller are highly reliable. Accordingly, the synthesized cross-section data D71 is generated by synthesizing the cross-section data D51 and D61, for example, using a synthesis technique of extracting right half data to the right of the center line H from the cross-section data D51, extracting left half data to the left of the center line H from the cross-section data D61 and joining these pieces of partial cross-section data at the edge of the center line H.

Subsequently, the cross-section graph generator 342 reconfigures the cross-section data D51, D61 generated first based on the top surface 111T side into data to be based on the bottom surface 111B side. FIG. 19A is a graph showing cross-section data D52 (second cross-section data) developed based on the bottom surface 111T side for the cross-section data D51. FIG. 19B is a graph showing cross-section data D62 (fourth cross-section data) developed based on the bottom surface 111T side for the cross-section data D61. Further, FIG. 19C shows cross-section data D72 obtained by synthesizing the cross-section data D52 and D62 by the data synthesizer 343.

The cross-section data D52 of FIG. 19A is thickness data whose diagonal bars on a side to the left of the vertical center line H of the silhouette E2 and at a luminance value of 4 or smaller are highly reliable as described in detail in the previous first example. On the other hand, the cross-section data D62 of FIG. 19B is thickness data whose diagonal bars on a side to the right of the vertical center line H of the silhouette E2 and at a luminance value of 4 or smaller are highly reliable. Accordingly, the synthesized cross-section data D72 is generated by synthesizing the cross-section data D52 and D62, for example, using a synthesis technique of extracting left half data to the left of the center line H from the cross-section data D52, extracting right half data to the right of the center line H from the cross-section data D62 and joining these pieces of partial cross-section data at the edge of the center line H.

The above cross-section data D71 and cross-section data D72 are further synthesized by the data synthesizer 343. FIG. 20 is a graph showing synthesized cross-section data D8 obtained by synthesizing the cross-section data D71 and D72. A synthesis technique, for example, is a technique of extracting data corresponding to substantially half on the top surface 111T side of the silhouette E2 from the cross-section data D71, extracting data corresponding to substantially half on the bottom surface 111B side of the silhouette E2 from the cross-section data D72 and synthesizing these pieces of data. Note that length data from the top surface 111T to the bottom surface 111B of the solder portion 111 is necessary to synthesize the cross-section data D71, D72. The data synthesizer 343 uses the third thickness data obtained from the third X-ray image to derive this length data.

The synthesized cross-section data D8 obtained as described above is cross-section data precisely representing the vertical cross-sectional shape of the solder portion 111 since it is a collection of highly reliable region data of the cross-section data D51, D52, D61 and D62. Actually, the synthesized cross-section data D8 coincides with a cross-sectional shape in which two objects having an elliptical cross-section are laminated, i.e. the silhouette E2 having a cross-sectional shape of a laminate of the bottom surface part 111a and the top surface part 111b.

Modifications (1) In the above embodiment, the example is shown in which the X-ray image located on the straight line A0 inclined by 45° with respect to the horizontal line and obtained in the 135° direction (first X-ray image) and the X-ray image located on the straight line A0 and obtained in the 315° direction (second X-ray image) are used. That is, the example is shown in which the cross-sectional shape on the straight line A0 passing a part with a largest diameter of the solder portion 101 having a circular horizontal cross-sectional shape is obtained. Instead of or in addition to this, cross-sectional shapes on a straight line passing an arbitrary part of the solder portion 101 may be obtained.

Figure 21:
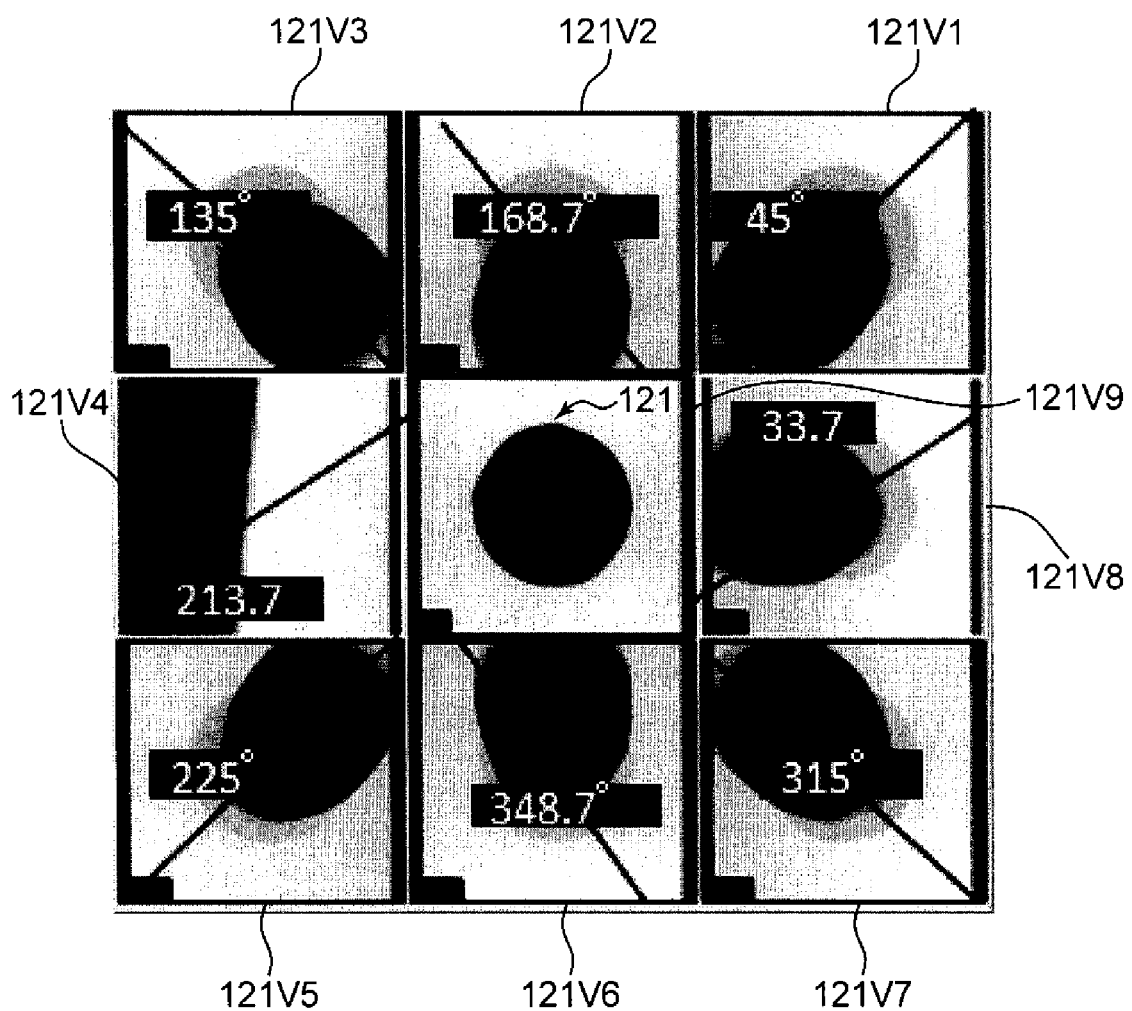
FIG. 21 is an array diagram of X-ray images showing a modification.

With reference to FIG. 21, here is shown an example in which a target 121 is imaged in eight directions. The target 121 is a cylindrical (rotationally symmetric) solid object, for example, like the solder portion 101. In the above embodiment, the example is shown in which a combination of an X-ray image 121V1 obtained in the 45° direction and an X-ray image 121V5 obtained in the opposite 225° direction or a combination of an X-ray image 121V3 obtained in the 135° direction and an X-ray image 121V7 obtained in the opposite 315° direction is used. Without being limited to this, a combination of an X-ray image 121V8 obtained in a 33.7° direction and an X-ray image 121V4 obtained in an opposite (parallel) 213.7° direction or a combination of an X-ray image 121V2 obtained in a 168.7° direction and an X-ray image 121V6 obtained in an opposite 348.7° direction may be used. In this case, length (height) information between the top surface and the bottom surface is also obtained on a straight line on which the cross-sectional shape is obtained.

(2) In the above embodiment, the example is shown in which the imaging elevation angle is set at 45°. The elevation angle may be set at an angle other than 45° and arbitrarily set in the range of 0° to 90°. Note that a diagram bar graph configuring the cross-section data changes an angle of inclination thereof according to the elevation angle. For example, if the elevation angle=60°, the cross-section graph generator 342 generates cross-section data with the angle of inclination of a diagonal bar graph set at 60°.

(3) If a target for X-ray inspection is a rotationally symmetric solid object like the solder portion 101, i.e. if a vertical cross-sectional shape of a good product is a cross-sectional shape of a rotationally symmetric solid object, the shape can be inspected regardless of imaging directions of obtained X-ray images combined. For example, a combination of the X-ray image 101V1 obtained in the 45° direction and the X-ray image 101V2 obtained in the 135° direction that is not opposite to the 45° direction may be used in the example of FIG. 9. Alternatively, the aforementioned first to fourth cross-section data may be extracted from the respective four X-ray images 101V1 to 101V4. Then, cross-section data of the highly reliable region may be partially extracted from these pieces of cross-section data and these extracted pieces of cross-section data may be synthesized into one piece of cross-section data by a technique similar to the above one.

(4) Although described also in the above embodiment, another electronic component or the like mounted on the printed circuit board W may be reflected as an obstacle depending on the position of the solder portion 101 if the solder portion 101 is imaged in a certain imaging direction. A technique of further synthesizing synthesized cross-section data obtained from a plurality of pairs of X-ray images can be used as a method for canceling the influence of this obstacle. This is described with an example in which the imaging controller 33 causes the printed circuit board W (solder portion 101) to be imaged in eight different directions, for example, as shown in FIG. 21. In this case, it is possible to obtain four pieces of synthesized cross-section data based on the X-ray images 121V1 and 121V5, the X-ray images 121V2 and 121V6, the X-ray images 121V3 and the 121V7 and the X-ray images 121V4 and 121V8.

Figure 22:
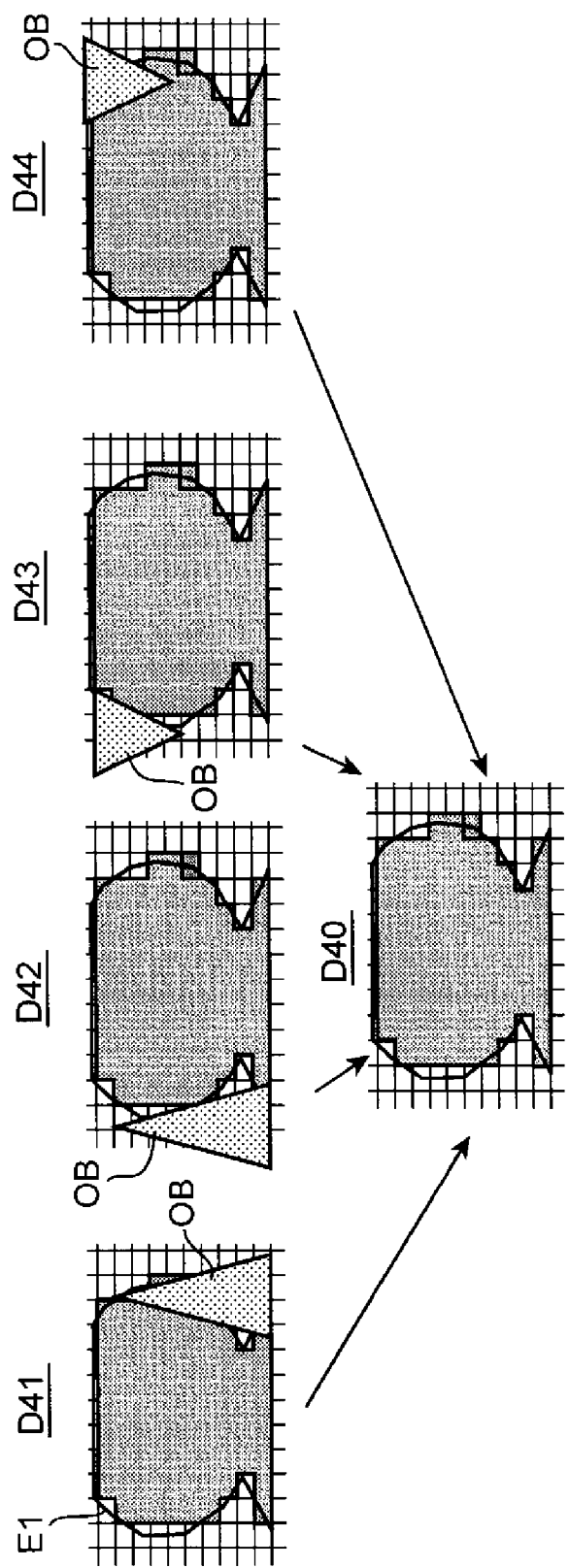
FIG. 22 is a diagram showing a synthesis example of cross-section data according to the modification.

FIG. 22 illustrates synthesized cross-section data D41, D42, D43 and D44 of the solder portion 101 as an example of the four pieces of synthesized cross-section data. It is assumed that an obstacle OB is reflected in each of these pieces of synthesized cross-section data. In each single piece of the synthesized cross-section data D41, D42, D43 and D44, the obstacle OB becomes a noise and precise vertical cross-section data of the solder portion 101 cannot be obtained.

However, in the case of further synthesizing the synthesized cross-section data D41, D42, D43 and D44, it is possible to generate synthesized cross-section data D40 in which the influence of the obstacle OB is eliminated. A synthesis technique adopted here may be a synthesis technique of overlapping the synthesized cross-section data D41, D42, D43 and D44 and, if at least one grid is a "white grid" out of grids of the overlapped four pieces of cross-section data, treating this grid as the "white grid". A position where the obstacle OB appears differs in the synthesized cross-section data D41, D42, D43 and D44. Accordingly, at a position where the obstacle OB appears in one piece of synthesized cross-section data, the grid is the "white grid" in the other pieces of synthesized cross-section data. Thus, by adopting this synthesis method, the cross-sectional shape of the solder portion 101 can be obtained without being influenced by the obstacle OB. Even if it is essential to image four pairs of images as described above, the imaging needs to be performed only eight times and the number of times of imaging can be sufficiently smaller as compared with conventional methods.

(5) An imaging direction in which an obstacle is reflected may be specified in the first imaging operation for a target and imaging in the imaging direction in which the obstacle is reflected may be omitted in the subsequent imaging operations for the target. An example is shown in which an obstacle is found to be reflected only in a pair of the X-ray images obtained in the 135° direction and the X-ray image obtained in the opposite 315° direction, but not to be reflected in pairs of X-ray images in the other directions in the imaging example of FIG. 21. In this case, imaging in the 135° direction and 315° direction is stopped thereafter. This can further reduce the number of times of imaging.

(6) In the above embodiment, the example is shown in which the highly reliable regions appear near the top surface 101T and the bottom surface 101B of the solder portion 101. However, depending on the imaging elevation angle, a highly reliable region may appear on the peripheral edge of an intermediate part between the top surface 101T and the bottom surface 101B. For example, in the case of imaging the barrel-shaped solder portion 101 directly from above (elevation angle of 90°), the vicinity of the peripheral edge of a vertically intermediate part is a region where the X-ray transmission length is shortest and this region becomes a highly reliable region. Accordingly, imaging may be performed in a first direction (elevation angle of 45°) and a second direction (elevation angle of 45°) which are different by 180° and also in a third direction in which an elevation angle is 90° and cross-section data of the highly reliable region may be extracted from X-ray images obtained by these three imaging operations. Alternatively, imaging may be performed at an elevation angle closer to 90° (e.g. an elevation angle of about 60°) in each of the first and second directions, and cross-section data of the highly reliable region may be extracted from X-ray images obtained by a total of four imaging operations, i.e. X-ray images obtained at two elevation angles in the first direction and those obtained at two elevation angles in the second direction. Of course, it is also possible to obtain images having different highly reliable regions by five or more imaging operations within such a range as not to perform imaging an excessive number of times, and extract cross-section data of the highly reliable regions from each X-ray image.

Description of Operation Flow

Figure 23:
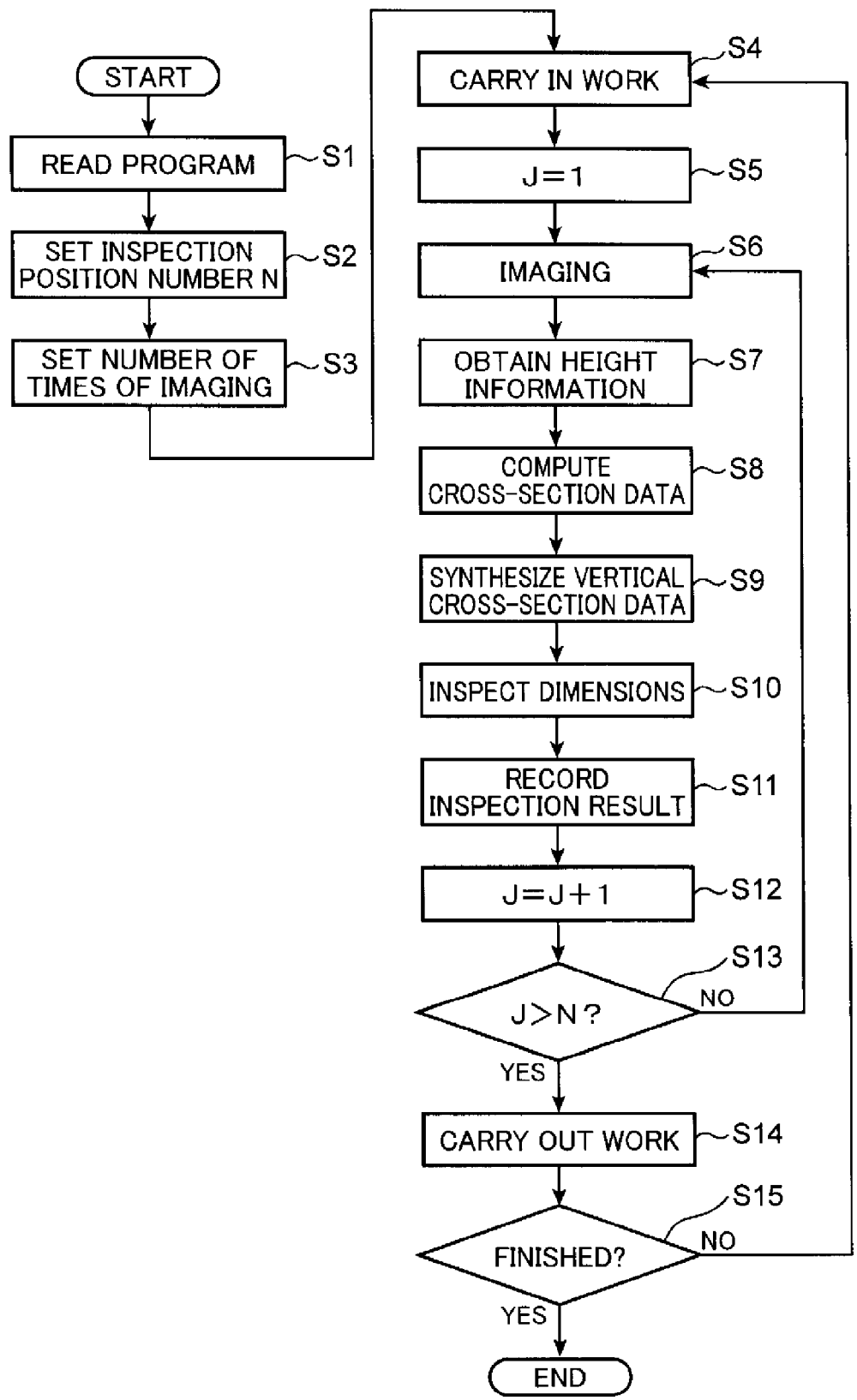
FIG. 23 is a flow chart showing the operation of the X-ray inspection device.

FIG. 23 is a flow chart showing the operation of the X-ray inspection device A. When an inspection is started, the overall controller 30A (see FIG. 2) receives the setting of the type of a target to be inspected. The type is, for example, a type corresponding to the type of the printed circuit board W, the type of the BGA 100 or the like. According to this type setting, the program switching processor 36 reads the discrimination program stored in the discrimination program storage 52 of the storage device 50 and corresponding to the inspection target (Step S1).

Further, the overall controller 30A receives the setting of an inspection position number N for the printed circuit board W, i.e. at how many positions the target is inspected for one printed circuit board W (Step S2) and the setting as to how many imaging operations are to be performed at each target position (Step S3). Thereafter, the printed circuit board W is carried into the housing 10 by the control of the conveyor controller 32 (Step S4) and placed on the stage 11. The printed circuit board W is positioned at an imaging position by the control of the stage controller 31.

Subsequently, the overall controller 30A sets an inspection execution counter J to 1 (Step S5). Then, the imaging controller 33 drives the X-ray radiation device 20 and the X-ray camera 21 via the X-ray radiation device driver unit 20a and the X-ray camera driver unit 21a, whereby the printed circuit board W (solder portion 101) is imaged a predetermined number of times in predetermined directions and at a predetermined elevation angle (Step S6). This imaging operation is, for example, composed of imaging in four directions spaced apart at an angular interval of 90° or imaging in eight directions spaced apart at an angular interval of 45° and imaging in the vertical direction to obtain the height information of the solder portion 101.

X-ray image data obtained by the above imaging operation is temporarily stored in an unillustrated memory and used for the data processing by the image processor 34. First, the thickness data computer 341 converts luminance values of the X-ray image imaged in each direction into thickness data by referring to the conversion table stored in the conversion data storage 51. Out of this thickness data, the height information (distance between the top surface 101T and the bottom surface 101B) of the solder portion 101 is obtained from the thickness data based on the X-ray image obtained by the imaging in the vertical direction (Step S7).

Subsequently, by the cross-section graph generator 342, diagonal bar graph data corresponding to vertical cross-section data of the solder portion 101 is generated based on all or some of the X-ray images obtained by the imaging in the four or eight directions (Step S8). Two pieces of the vertical cross-section data are generated based on each of the top surface 101T side and the bottom surface 101B side of the solder portion 101, for example, as illustrated in FIGS. 10, 11, 13 and 14. Then, as illustrated in FIGS. 12, 15 and 16, the data synthesizer 343 extracts cross-section data of a highly reliable region from each piece of the vertical cross-section data and synthesizes these extracted pieces, thereby generating synthesized cross-section data of one solder portion 101 (Step S9).

Subsequently, the quality determination processor 35 determines to which category of a good product and a defective product the shape of the inspection target belongs by comparing a shape based on the synthesized cross-section data obtained in Step S9 and a shape as a basis for the good product (Step S10). This determination result is stored in the unillustrated memory in association with identification information of the solder 101 as the inspection target (Step S11).

Thereafter, the overall controller 30A increments the inspection execution counter J (Step S12) and determines whether or not the counter value is larger than the inspection position number N set for this printed circuit board W (Step S13). If there remains any position to be inspected (NO in Step S13), a return is made to Step S6 and a process of Steps S6 to S11 is repeated for the next inspection position. On the other hand, if the inspection of all the inspection positions is completed (YES in Step S13), the printed circuit board W is carried out to the outside of the housing 10 by the control of the stage controller 31 and the conveyor controller 32 (Step S14).

Then, it is confirmed whether or not there is any succeeding printed circuit board W (Step S15). If there is any (NO in Step S15), a return is made to Step S4, a new printed circuit board W is carried into the housing 10 and the processing similarly to the above is repeated. Contrary to this, if there is no succeeding printed circuit board W, the process is finished.

Although the embodiment of the present disclosure has been described above, the present disclosure is not limited to the above embodiment. For example, in the above embodiment, the solder portion 101 that is a melt of the solder ball 103 is mainly illustrated as a target for X-ray inspection. The target may be an object other than the solder portion 101 or may be one of various components, molded articles, processed articles, foods, tablets and the like. Further, articles having a rotationally symmetric three-dimensional shape are preferable targets of the present disclosure, but articles having a three-dimensional shape that is not rotationally symmetric may also be inspection targets.

Note that the specific embodiment described above mainly includes disclosures having the following configurations.

An X-ray inspection method according to one aspect of the present disclosure is an X-ray inspection method for computing a cross-sectional shape of a three-dimensional target having a first surface and a second surface facing the first surface by transmitting X-rays through the target using an X-ray source for radiating X-rays, an X-ray detector for detecting the X-rays and a computing device. The X-ray source is arranged in a predetermined first direction and at a predetermined first elevation angle with respect to the target, the X-ray detector is arranged to face the X-ray source across the target and, in this state, the X-rays are radiated from the X-ray source and a first X-ray image of the target is obtained by the X-ray detector. The X-ray source is arranged in a second direction different from the first direction and at a predetermined second elevation angle with respect to the target, the X-ray detector is arranged to face the X-ray source across the target and, in this state, X-rays are radiated from the X-ray source and a second X-ray image of the target is obtained by the X-ray detector. The computing device is caused to compute first thickness data of the target viewed in the first direction and in a direction of the first elevation angle based on a luminance value distribution of the first X-ray image along the first direction and further compute first cross-section data based on the first surface side of the target and second cross-section data based on the second surface side based on the first thickness data. The computing device is caused to compute second thickness data of the target viewed in the second direction and in a direction of the second elevation angle based on a luminance value distribution of the second X-ray image along the second direction and further compute third cross-section data based on the first surface side of the target and fourth cross-section data based on the second surface side based on the second thickness data. The computing device is caused to partially extract cross-section data of a highly reliable region determined by the first and second directions from the first to fourth cross-section data and derive cross-section data of the target by synthesizing the extracted pieces of partial cross-section data.

According to this method, the cross-section data of the target can be obtained based on two X-ray images imaged for the target, i.e. the first X-ray image imaged in the first direction (at the first elevation angle) and the second X-ray image imaged in the second direction (at the second elevation angle). This is realized by a process of converting the first and second X-ray images into the first and second thickness data, obtaining the first and second cross-section data and the third and fourth cross-section data from the respective pieces of the thickness data and partially extracting and synthesizing the cross-section data of the highly reliable region from these obtained pieces of cross-section data. Since the obtained cross-section data represents a synthesis of the highly reliable regions of the first to fourth cross-section data, accuracy is ensured. Note that a typical example of the cross-section data of the highly reliable region is cross-section data of a region corresponding to a part having a relatively short X-ray transmission length.

In the above method, preferably, the first and second directions are directions opposite to each other and the first and second elevation angles are the same angle.

According to this method, the cross-section data along one cross-section line can be obtained. Further, since the elevation angles of both directions are equal, the process of synthesizing the first to fourth cross-section data can be simplified.

In the above method, preferably, the computing device includes conversion data representing a relationship of the thickness of the target and a luminance when X-rays are transmitted and formatted into a table in advance and is caused to compute the first and second thickness data by performing a process of converting luminance values of the first and second X-ray images along the first and second directions into thicknesses based on the conversion data.

According to this method, the first and second thickness data can be quickly computed since the table corresponding to an X-ray absorption characteristic of the target is prepared in advance.

In this case, the X-ray source may be arranged to face the first surface of the target, the X-ray detector may be arranged to face the second surface of the target and, in this state, X-rays may be radiated from the X-ray source and a third X-ray image of the target may be obtained by the X-ray detector. The computing device may be caused to compute length data from the first surface to the second surface of the target by converting luminance values of the third X-ray image into thicknesses based on the conversion data and determine a thickness between the first and second surfaces of the target by referring to the length data when the pieces of partial cross-section data are synthesized.

In synthesizing the first and third cross-section data based on the first surface of the target and the second and fourth cross-section data based on the second surface of the target, thickness data between the first and second surfaces is necessary. The third X-ray image imaged with the X-ray source and the X-ray detector arranged to face the first and second surfaces (elevation angle of 90°) reflects a degree of X-ray absorption corresponding to the thickness of the target and the length from the first surface to the second surface can be precisely computed based on the conversion data.

In the above method, preferably, when the target has a rotationally symmetric three-dimensional shape, the X-ray source and the X-ray detector are caused to obtain a plurality of pairs of the first and second X-ray images by a combination of directions different from the first and second directions in addition to a combination of the first and second directions and the computing device is caused to partially extract cross-section data of a highly reliable region from the first to fourth cross-section data respectively obtained from the plurality of pairs of the first and second X-ray images and derive the cross-section data of the target by synthesizing the extracted pieces of partial cross-section data.

When the target has a rotationally symmetric three-dimensional shape, the same cross-section data is basically obtained regardless of in which direction the target is imaged. This means that any X-ray image can be used for the partial cross-section data synthesis regardless of in which direction the X-ray image is imaged. According to the above method, the number of the imaged X-ray images is slightly increased, but options of the cross-section data of the highly reliable region during the partial cross-section data synthesis can be increased. For example, even if an obstacle is reflected in an X-ray image imaged in a certain direction, the influence of that obstacle can be eliminated.

Further, preferably, when the target has a rotationally symmetric three-dimensional shape and an obstacle is present near the target, the X-ray source and the X-ray detector are caused to obtain a plurality of pairs of the first and second X-ray images by a combination of directions different from the first and second directions in addition to a combination of the first and second directions and the computing device is caused to partially extract cross-section data of a highly reliable region from the first to fourth cross-section data respectively obtained from the plurality of pairs of the first and second X-ray images, derive a plurality of pieces of synthesized cross-section data by synthesizing the extracted pieces of partial cross-section data for each pair and subsequently derive the cross-section data of the target, in which the influence of the obstacle is eliminated, by synthesizing the plurality of derived pieces of synthesized cross-section data.

According to the above method, even if an obstacle is present near the target, the influence of the obstacle can be eliminated by performing a process of further synthesizing the pieces of synthesized cross-section data respectively obtained from the plurality of pairs of the first and second X-ray images.

In the above method, it is one of the most preferable modes of the X-ray inspection method according to the present disclosure that the target is a solder connecting portion that connects an electronic component and a board and contains a melt of a solder ball.

An X-ray inspection device according to another aspect of the present disclosure is an X-ray inspection device for computing a cross-sectional shape of a three-dimensional target having a first surface and a second surface facing the first surface by transmitting X-rays through the target and includes an X-ray source for radiating X-rays, an X-ray detector for detecting the X-rays radiated from the X-ray source and transmitted through the target and obtaining an X-ray image, a drive controller for controlling the operation of the X-ray source and the X-ray detector, an image processor for computing thickness data of the target based on a luminance value distribution of the X-ray image and computing cross-section data of the target based on the thickness data, and a determiner for determining whether or not the shape of the target is good based on the cross-section data. The drive controller causes the X-ray source to be arranged in a predetermined first direction and at a predetermined first elevation angle with respect to the target, causes the X-ray detector to be arranged to face the X-ray source across the target and, in this state, causes the X-rays to be radiated from the X-ray source and causes the X-ray detector to obtain a first X-ray image of the target. Subsequently, the drive controller causes the X-ray source to be arranged in a second direction different from the first direction and at a predetermined second elevation angle with respect to the target, causes the X-ray detector to be arranged to face the X-ray source across the target and, in this state, causes X-rays to be radiated from the X-ray source and causes the X-ray detector to obtain a second X-ray image of the target. The image processor computes first thickness data of the target viewed in the first direction and in a direction of the first elevation angle based on a luminance value distribution of the first X-ray image along the first direction and further computes first cross-section data based on the first surface side of the target and second cross-section data based on the second surface side based on the first thickness data. Subsequently, the image processor computes second thickness data of the target viewed in the second direction and in a direction of the second elevation angle based on a luminance value distribution of the second X-ray image along the second direction and further computes third cross-section data based on the first surface side of the target and fourth cross-section data based on the second surface side based on the second thickness data. Further, the image processor partially extracts cross-section data of a highly reliable region determined by the first and second directions from the first to fourth cross-section data and derives the cross-section data of the target by synthesizing the extracted pieces of partial cross-section data.

According to this configuration, the cross-section data of the target can be obtained based on two X-ray images imaged for the target, i.e. the first X-ray image imaged in the first direction (at the first elevation angle) and the second X-ray image imaged in the second direction (at the second elevation angle). This is realized by a process of converting the first and second X-ray images into the first and second thickness data, obtaining first and second cross-section data and the third and fourth cross-section data from the respective pieces of the thickness data and partially extracting and synthesizing the cross-section data of the highly reliable region from these pieces of cross-section data. Since the obtained cross-section data represents a synthesis of the highly reliable regions of the first to fourth cross-section data, accuracy is ensured.

In the above configuration, preferably, a storage is further provided which stores conversion data representing a relationship of the thickness of the target and a luminance when X-rays are transmitted and formatted into a table in advance, and the image processor computes the first and second thickness data by converting luminance values of the first and second X-ray images along the first and second directions into thicknesses based on the conversion data.

According to this configuration, the image processor can quickly compute the first and second thickness data by referring to the storage since the storage storing the table corresponding to an X-ray absorption characteristic of the target in advance is included.

As described above, according to the present disclosure, it is possible to provide an X-ray inspection method and a device capable of precisely obtaining cross-section data of an inspection target based on as few X-ray images as possible, i.e. by reducing the number of times of imaging the inspection target as much as possible.

The invention claimed is:
1. An X-ray inspection method for computing a cross-sectional shape of a three-dimensional target having a first surface and a second surface facing the first surface by transmitting X-rays through the target using an X-ray source for radiating X-rays, an X-ray detector for detecting the X-rays and a computing device, comprising:
   arranging the X-ray source in a predetermined first direction and at a predetermined first elevation angle with respect to the target and the X-ray detector to face the X-ray source across the target and, in this state, causing the X-rays to be radiated from the X-ray source and the X-ray detector to obtain a first X-ray image of the target;
   arranging the X-ray source in a second direction different from the first direction and at a predetermined second elevation angle with respect to the target and the X-ray detector to face the X-ray source across the target and, in this state, causing X-rays to be radiated from the X-ray source and the X-ray detector to obtain a second X-ray image of the target;
   causing the computing device to compute first thickness data of the target viewed in the first direction and in a direction of the first elevation angle based on a luminance value distribution of the first X-ray image along the first direction and further compute first cross-section data based on the first surface of the target and second cross-section data based on the second surface based on the first thickness data;
   causing the computing device to compute second thickness data of the target viewed in the second direction and in a direction of the second elevation angle based on a luminance value distribution of the second X-ray image along the second direction and further compute third cross-section data based on the first surface of the target and fourth cross-section data based on the second surface based on the second thickness data; and
   causing the computing device to partially extract cross-section data of a highly reliable region determined by the first and second directions from the first to fourth cross- section data and derive cross-section data of the target by synthesizing the extracted pieces of partial cross-section data.

2. The X-ray inspection method according to claim 1, wherein:
the first and second directions are directions opposite to each other; and
the first and second elevation angles are the same angle.

3. The X-ray inspection method according to claim 1, wherein the computing device:
includes conversion data representing a relationship of the thickness of the target and a luminance when X-rays are transmitted and formatted into a table in advance; and
is caused to compute the first and second thickness data by performing a process of converting luminance values of the first and second X-ray images along the first and second directions into thicknesses based on the conversion data.

4. The X-ray inspection method according to claim 3, wherein:
the X-ray source is arranged to face the first surface of the target, the X-ray detector is arranged to face the second surface of the target and, in this state, X-rays are radiated from the X-ray source and a third X-ray image of the target is obtained by the X-ray detector; and
the computing device is caused to compute length data from the first surface to the second surface of the target by converting luminance values of the third X-ray image into thicknesses based on the conversion data and determine a thickness between the first and second surfaces of the target by referring to the length data when the pieces of partial cross-section data are synthesized.

5. The X-ray inspection method according to claim 1, wherein:
when the target has a rotationally symmetric three-dimensional shape,
the X-ray source and the X-ray detector are caused to obtain a plurality of pairs of the first and second X-ray images by a combination of directions different from the first and second directions in addition to a combination of the first and second directions; and
the computing device is caused to partially extract cross-section data of a highly reliable region from the first to fourth cross-section data respectively obtained from the plurality of pairs of the first and second X-ray images and derive the cross-section data of the target by synthesizing the extracted pieces of partial cross-section data.

6. The X-ray inspection method according to claim 1, wherein:
when the target has a rotationally symmetric three-dimensional shape and an obstacle is present near the target,
the X-ray source and the X-ray detector are caused to obtain a plurality of pairs of the first and second X-ray images by a combination of directions different from the first and second directions in addition to a combination of the first and second directions; and
the computing device is caused to partially extract cross-section data of a highly reliable region from the first to fourth cross-section data respectively obtained from the plurality of pairs of the first and second X-ray images, derive a plurality of pieces of synthesized cross-section data by synthesizing the extracted pieces of partial cross-section data for each pair and subsequently derive the cross-section data of the target, in which the influence of the obstacle is eliminated, by synthesizing the plurality of derived pieces of synthesized cross-section data.

7. The X-ray inspection method according to claim 1, wherein:
the target is a solder connecting portion that connects an electronic component and a board and contains a melt of a solder ball.

8. An X-ray inspection device for computing a cross-sectional shape of a three-dimensional target having a first surface and a second surface facing the first surface by transmitting X-rays through the target, comprising:
an X-ray source for radiating X-rays;
an X-ray detector for detecting the X-rays radiated from the X-ray source and transmitted through the target and obtaining an X-ray image;
a drive controller configured to control the operation of the X-ray source and the X-ray detector;
an image processor for computing thickness data of the target based on a luminance value distribution of the X-ray image and computing cross-section data of the target based on the thickness data; and
a determiner configured to determine whether or not the shape of the target is good based on the cross-section data;
wherein:
the drive controller:
causes the X-ray source to be arranged in a predetermined first direction and at a predetermined first elevation angle with respect to the target, causes the X-ray detector to be arranged to face the X-ray source across the target and, in this state, causes the X-rays to be radiated from the X-ray source and causes the X-ray detector to obtain a first X-ray image of the target, and
subsequently causes the X-ray source to be arranged in a second direction different from the first direction and at a predetermined second elevation angle with respect to the target, causes the X-ray detector to be arranged to face the X-ray source across the target and, in this state, causes X-rays to be radiated from the X-ray source and causes the X-ray detector to obtain a second X-ray image of the target; and
the image processor:
computes first thickness data of the target viewed in the first direction and in a direction of the first elevation angle based on a luminance value distribution of the first X-ray image along the first direction and further computes first cross-section data based on the first surface side of the target and second cross-section data based on the second surface side based on the first thickness data,
subsequently computes second thickness data of the target viewed in the second direction and in a direction of the second elevation angle based on a luminance value distribution of the second X-ray image along the second direction and further computes third cross-section data based on the first surface side of the target and fourth cross-section data based on the second surface side based on the second thickness data, and
further partially extracts cross-section data of a highly reliable region determined by the first and second directions from the first to fourth cross-section data and derives the cross-section data of the target by synthesizing the extracted pieces of partial cross-section data.

9. The X-ray inspection device according to claim 8, further comprising a storage for storing conversion data representing a relationship of the thickness of the target and a luminance when X-rays are transmitted and formatted into a table in advance, wherein the image processor computes the first and second thickness data by converting luminance values of the first and second X-ray images along the first and second directions into thicknesses based on the conversion data.

* * * * *